US010888633B2

(12) United States Patent
Lynch et al.

(10) Patent No.: US 10,888,633 B2
(45) Date of Patent: *Jan. 12, 2021

(54) PHASE-STABLE, SPRAYABLE FRESHENING COMPOSITIONS COMPRISING SUSPENDED PARTICLES

(71) Applicant: The Procter & Gamble Company, Cincinnati, OH (US)

(72) Inventors: Matthew Lawrence Lynch, Mariemont, OH (US); Carla Jean Colina, Cincinnati, OH (US); Steven Anthony Horenziak, Cincinnati, OH (US); Brandon Philip Illie, Felicity, OH (US); Yonas Gizaw, West Chester, OH (US); Yiping Sun, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,040

(22) Filed: Sep. 10, 2018

(65) Prior Publication Data
US 2019/0001012 A1    Jan. 3, 2019

Related U.S. Application Data

(63) Continuation of application No. 15/660,997, filed on Jul. 27, 2017, now Pat. No. 10,143,764.

(60) Provisional application No. 62/369,311, filed on Aug. 1, 2016.

(51) Int. Cl.
*A61L 9/012* (2006.01)
*A61L 9/01* (2006.01)
*A61L 2/22* (2006.01)
*C11B 9/00* (2006.01)
*A01N 25/10* (2006.01)
*A61L 9/14* (2006.01)
*B01J 12/02* (2006.01)
*B01J 13/02* (2006.01)

(52) U.S. Cl.
CPC .............. *A61L 9/012* (2013.01); *A01N 25/10* (2013.01); *A61L 2/22* (2013.01); *A61L 9/01* (2013.01); *A61L 9/14* (2013.01); *B01J 13/02* (2013.01); *C11B 9/00* (2013.01)

(58) Field of Classification Search
None
See application file for complete search history.

(56) References Cited

U.S. PATENT DOCUMENTS

| | | | |
|---|---|---|---|
| 4,369,125 A | 1/1983 | Kragen et al. | |
| 5,171,564 A | 12/1992 | Nathoo | |
| 5,234,915 A * | 8/1993 | Mathur | A61F 13/15252 514/449 |
| 5,498,436 A * | 3/1996 | Modliszewski | A23C 19/0765 426/573 |
| 5,670,077 A | 9/1997 | Carlson | |
| 5,714,137 A | 2/1998 | Trinh et al. | |
| 5,872,088 A | 2/1999 | Pucci et al. | |
| 7,119,055 B2 | 10/2006 | Cheung et al. | |
| 7,288,512 B2 | 10/2007 | Boone et al. | |
| 8,039,015 B2 | 10/2011 | Speaker et al. | |
| 8,222,193 B2 | 7/2012 | Tanaka et al. | |
| 8,329,154 B2 | 12/2012 | Uchiyama et al. | |
| 10,076,583 B2 | 9/2018 | Lynch et al. | |
| 10,076,586 B2 | 9/2018 | Lynch et al. | |
| 10,080,814 B2 | 9/2018 | Lynch et al. | |
| 10,113,140 B2 | 10/2018 | Frankenbach | |
| 10,143,764 B2 | 12/2018 | Lynch et al. | |
| 2002/0143172 A1* | 10/2002 | Ookawa | C08B 15/02 536/56 |
| 2004/0131645 A1* | 7/2004 | Williams | A61K 8/042 424/400 |
| 2005/0022382 A1 | 2/2005 | Bruck et al. | |
| 2006/0039939 A1* | 2/2006 | Lai | C08F 2/38 424/401 |
| 2006/0045851 A1 | 3/2006 | Fitzgerald | |
| 2007/0202063 A1 | 8/2007 | Dihora et al. | |
| 2010/0034757 A1 | 2/2010 | Fujii | |
| 2010/0280231 A1 | 11/2010 | Nakano | |
| 2013/0157922 A1* | 6/2013 | Mikkelsen | A61L 9/012 512/4 |
| 2015/0104348 A1* | 4/2015 | Nichols | A61L 9/01 422/5 |

(Continued)

FOREIGN PATENT DOCUMENTS

EP    1637188 A1    3/2006
GB    2 363 386 A    12/2001

(Continued)

OTHER PUBLICATIONS

Fei et al. "Microencapsulation mechanism and size control of fragrance microcapsules with melamine resin shell". 2015.*
https://hero-clean.com/products/odor-eliminating-spray/; website downloaded Sep. 20, 2016.
http://www.wonderfresh.com/ ; website downloaded Sep. 20, 2016.
Macromolecules 1995, Stoichiometry and Conformation of Xanthan in Synergistic Gelation with Locust Bean Gum or Konjac Glucomannan: Evidence for Heterotypic Binding; F. M. Goycoolea; 13 Pages.
Carbohydrate Polymers 14 (1991); Influence of the Acetyl Substituent on the Interaction of Xanthan with Plant Polysaccharides—In. Xanthan-Konjac Mannan Systems; Karolyn P. Shatwell; 17 Pages.
ScienceDirect; food Hydrocolloids 22 (2008); Synergistic binding of konjac glucomannan to xanthan on mixing at room temperature; Sinead M. Fitzsimons: 11 Pages.

(Continued)

*Primary Examiner* — Danah Al-Awadi
(74) *Attorney, Agent, or Firm* — Abbey A. Lopez

(57) ABSTRACT

A freshening composition is provided. The composition includes at least one particle, and an aqueous carrier. The composition includes a polysaccharide system having a first polysaccharide and a second polysaccharide. The first polysaccharide is xanthan gum and the second polysaccharide is selected from the group consisting of konjac gum, locust bean gum, and combinations thereof. The composition may include an unencapsulated perfume.

12 Claims, 5 Drawing Sheets

(56) References Cited

U.S. PATENT DOCUMENTS

| | | | |
|---|---|---|---|
| 2015/0351519 A1 | 12/2015 | Dring et al. | |
| 2016/0193122 A1* | 7/2016 | Lei | A61K 8/11 424/401 |
| 2018/0028706 A1 | 2/2018 | Lynch et al. | |
| 2019/0001013 A1 | 1/2019 | Lynch et al. | |

FOREIGN PATENT DOCUMENTS

| | | |
|---|---|---|
| GB | 2440214 A | 1/2008 |
| JP | H10-88196 A | 4/1998 |
| WO | WO 2001/27236 A1 | 4/2001 |
| WO | WO 2001/60961 A1 | 8/2001 |
| WO | WO 2003/89019 A1 | 10/2003 |
| WO | WO 2003/89561 A2 | 10/2003 |
| WO | WO 2004/74421 A | 9/2004 |
| WO | WO 2004/74422 A | 9/2004 |
| WO | WO 2005/025626 A2 | 3/2005 |
| WO | WO 2006/18694 A1 | 2/2006 |
| WO | WO 2007/61685 A1 | 5/2007 |
| WO | WO 2011/89709 A1 | 7/2011 |
| WO | WO2013034871 A1 | 3/2013 |
| WO | WO2014161714 A1 | 10/2014 |
| WO | WO 2014/193908 A1 | 12/2014 |
| WO | W02016049398 A1 | 3/2016 |
| WO | WO2016049398 A1 | 3/2016 |

OTHER PUBLICATIONS

Carbohydrate Polymers 83 (2011 ); Studies on macromolecular interactions in ternary mixtures of konjac glucomannan, xanthan gum and sodium alginate; Stephen E. Harding; 10 Pages.
Molecular Weight Effects on Gelation and Rheological Properties of Konjac Glucomannan-Xanthan Mixtures; Received Jul. 27, 2009: revised Oct. 12, 2009: accepted Oct. 13, 2009; Dan Shen; 9 Pages.
Macromolecules; Stoichiometry and Conformation of Xanthan in Synergistic Gelation with Locust Bean Gum or Konjac Glucomannan: Evidence for Heterotypic Binding; Downloaded from http://pubs,acs,org on Apr. 29, 2009; F. M. Goycoolea; 14 Pages.
Macromolecules 1994; Interaction in Xanthan:—Glucomannan Mixtures and the Influence of Electrolyte; P. ADnable; 8 Pages.
ScienceDirect; Food Research International 40 (2007); Rheological study of xanthan and locust bean gum interaction in dilute solution: Effect of salt; J. Higiro; 13 Pages.
Biomacromolecules 2002; Xanthan and Glucomannan Mixtures: Synergistic Interactions and Gelation; Gaio Paradossi; 7 Pages.
ScienceDirect; Inlematiooul Journal of Phntmnccutics 349 (2008); Konjac glucomannan and konjac glucomannanlxanthan gum mixtures as excipients for controlled drug delivery systems. Diffusion of small drugs; Felipe Aivarez-Manceñido; 7 pages.
Food Hydrocolloids vol. 4 No. 6 pp. 489-493. 1991; Synergistic Interaction or xanthan gum with glucomannans and galactomannans; P.A.Williams; 5 pages.
A. Imeson (ed.), Thickming and Gelling Agents for Food, © Chapman & Hall 1997; Konjac gum; W.R. Thomas; 6 Pages.
Carbohydrate Po{ vmers 17 (1992); Role of conformation and acetylation of xanthan on xanthan-guar interaction; L Lopes; 6 pages.
Food Hydrocolloids 48 (2015); Analysis of deacetylated konjac glucomannan and xanthan gum phase separation by film forming; Weiping Jin; 7 Pages.
ScienceDirect; International Journal of Pharmaceutices 349 (2008); Konjac glucomannan and konjac glucomannanlxanthan gum mixtures as excipients for controlled drug delivery systems. Diffusion of small drugs; Felipe Alvarez-Manceñido; 8 Pages.
ScienceDirect; Carbohydrnte Polymers 69 (2007); "Melt-in-themouth" gels from mixtures of xanthan and konjac glucomannan under acidic conditions: A rheological and calorimetric study of the mechanism of synergistic gelation; A.A. Agoub; 12 Pages.
Carbohydrate Polymers 92 (2013); Control of the properties ofxanthan/ glucomannan mixed gels by varying xanthan fine structure; P. Fitzpatrick; 8 pages.
Carbohydrate Reaserch 176 (1988); Evidence for Intermolecular binding between xanthan end the glucomennan konjac mannan; Geoffrey J. Brownsey; 6 Pages.
Carbohydrate Polymers 144 (2016); New insights into xanthan synergistic interactions with konjac glucomannan: A novel interaction mechanism proposal; A. Abbaszadeh; 10 Pages.
PCT Search Report dated Oct. 27, 2017; PCT/US2017/044136; 13 Pages.
PCT Search Report dated Oct. 27, 2017; PCT/US2017/044135; 14 Pages.
PCT Search Report dated Oct. 27, 2017; PCT/US2017/044130; 14 Pages.
All Office Actions, U.S. Appl. No. 16/126,058.

* cited by examiner

PHASE-STABLE, SPRAYABLE FRESHENING COMPOSITIONS COMPRISING SUSPENDED PARTICLES

FIELD

The present disclosure relates to phase-stable, sprayable freshening compositions having a plurality of suspended particles.

BACKGROUND

There is a continued demand for long-lasting and/or controlled freshness on surfaces and in the air. Various different product forms exist to deliver freshness to surfaces, such as clothing, furniture, and the like, and to the air. For example, freshness products may take the form of candles, sprays, manual, automatic, and passive air freshener dispensers, laundry detergents, laundry enhancers, and dryer sheets, and various other forms. Sprayable compositions exist that attempt to deliver long lasting-freshness with relatively high levels of perfumes to mask or react with malodors, malodor counteractants that trap or react with malodors, and/or pro-perfumes. Various laundry products exist on the market that incorporate benefit delivery particles, such as encapsulated perfume particles for controlled release of perfume. Encapsulating the perfume provides delayed release of the perfume until the capsule breaks upon movement, such as being rubbed by a hand or across a fabric. Therefore, the perfume capsules can release perfume days or weeks after the perfume capsules are delivered to the fabric or surface.

Attempts have been made to provide sprayable compositions comprising perfume capsules because sprayable compositions provide a way for a user to quickly and easily apply a freshening composition to a particular surface. Exemplary products include HERO™ Clean and WONDER FRESH™ sprays. However, these products do not stabilize the perfume capsules in the compositions, resulting in the perfume capsules floating to the top of the composition. Before spraying the composition, such products require the user to shake the product to mix the perfume capsules with the liquid portion of the composition. This method may add extra time and effort for the user, and, additionally, may not result in an even distribution of the perfume capsules in the spray. If the perfume capsules are not evenly distributed in the liquid, some sprayed compositions may have a higher or lower concentration of perfume capsules than other sprays, resulting in inconsistent delivery of freshness to the air or surface.

Attempts have been made to suspend various different particles in compositions for different purposes. However, such attempts have included structurant systems that may not be sprayable. For example, such compositions may be very viscous and may result in large spray droplets when sprayed from a spray dispenser or may not be sprayable at all. Such compositions may not be acceptable to a user from an appearance standpoint. Such compositions may also not deliver a uniform distribution of the product onto a surface, which may negatively affect the performance of the product, including resulting in surface staining, surface residue, or inconsistent scent distribution. These structurant systems may also leave behind a residue after the composition dries on a surface.

Therefore, there is a need to provide a sprayable composition that delivers long-lasting or controlled freshness to a surface. There is a need to deliver a sprayable composition comprising benefit delivery particles that remain suspended in the composition. There is also a need to provide a sprayable product comprising benefit delivery particles that delivers a uniform distribution of small spray droplets with minimal residue.

SUMMARY

"Combinations"

A. A freshening composition comprising:
   a plurality of particles;
   a polysaccharide system comprising a first polysaccharide and a second polysaccharide, wherein the first polysaccharide is xanthan gum, and wherein the second polysaccharide is selected from the group consisting of konjac gum, locust bean gum, and combinations thereof; and
   an aqueous carrier.

B. The according to Paragraph A, wherein the first polysaccharide is present at a level of greater than 10 wt. % and less than 90 wt. %, preferably 20 wt. % to 80 wt. %, more preferably 40 wt. % to 60 wt. %, by weight of the polysaccharide system.

C. The composition according to any of the preceding paragraphs, wherein the polysaccharide system has a weight-average molecular weight in the range of 10,000 Daltons to 15,000,000 Daltons, preferably 200,000 Daltons to 10,000,000 Daltons, more preferably 300,000 Daltons to 6,000,000 Daltons, most preferably 300,000 Daltons to 500,000 Daltons.

D. The composition according to any of the preceding paragraphs, wherein the total polysaccharide level of the composition is less than 0.5 wt. %, by weight of the composition, preferably less than 0.2 wt. %, more preferably less than 0.1 wt. %, more preferably less than 0.08 wt. %, and most preferably less than 0.06 wt. %.

E. The composition according to any of the preceding paragraphs, wherein the plurality of particles comprises a plurality of benefit agent delivery particles having a benefit agent and a wall material encapsulating the benefit agent.

F. The composition according to Paragraph E, wherein the wall material of the plurality of benefit agent delivery particles comprises one or more cationic, nonionic and/or anionic coatings.

G. The composition according to Paragraph E or Paragraph F, wherein the wall material of the plurality of benefit agent delivery particles comprises a material selected from the group consisting of: a polymer of acrylic acid or derivatives thereof, melamine formaldehyde, polyuria, and mixtures thereof.

H. The composition according to any of Paragraphs E through Paragraph G, wherein the composition comprises from 0.001 wt. % to 2.0 wt. % of the benefit agent, by weight of the composition.

I. The composition according to any of Paragraphs E through Paragraph H, wherein the benefit agent comprises a material selected from the group consisting of: a perfume mixture, a malodor counteractant, an antimicrobial agent, an insect repellant, and combinations thereof.

J. The composition according to any of Paragraphs E through Paragraph I, wherein the plurality of benefit agent delivery particles have an average longest projected dimension of 0.1 μm to 500 μm, preferably 1 micrometer to 100 micrometers, more preferably 5 micrometers to 50 micrometers, most preferably less than 100 micrometers.

K. The composition according to any of the preceding paragraphs further comprising a surface tension reducing agent, wherein the surface tension reducing agent is selected from the group consisting of: quaternary ammonium compounds, non-ionic surfactants, anionic surfactants, silicon compounds, and combinations thereof.

L. The composition according to any of the preceding paragraphs further comprising a malodor counteractant, wherein the malodor counteractant is selected from the group consisting of: polyols, cyclodextrin and derivatives thereof, amine functional polymers, aldehydes, and combinations thereof.

M. The composition according to any of the preceding paragraphs, wherein the composition comprises from 0.015 wt. % to 2.0 wt. % of unencapsulated perfume, preferably 0.01 wt. % to 1.0 wt. %, by weight of the composition.

N. The composition according to any of the preceding paragraphs, wherein the composition has an ionic strength of less than 0.02 mol/L, wherein the polysaccharide system has an average ratio of acetylation of 2.0 to 0.5, preferably 1.5 to 0.5.

O. The composition according to any of the preceding paragraphs, wherein the composition comprises 85 wt. % to 99.5 wt. % of the aqueous carrier, by weight of the composition.

DETAILED DESCRIPTION

Figure 1:
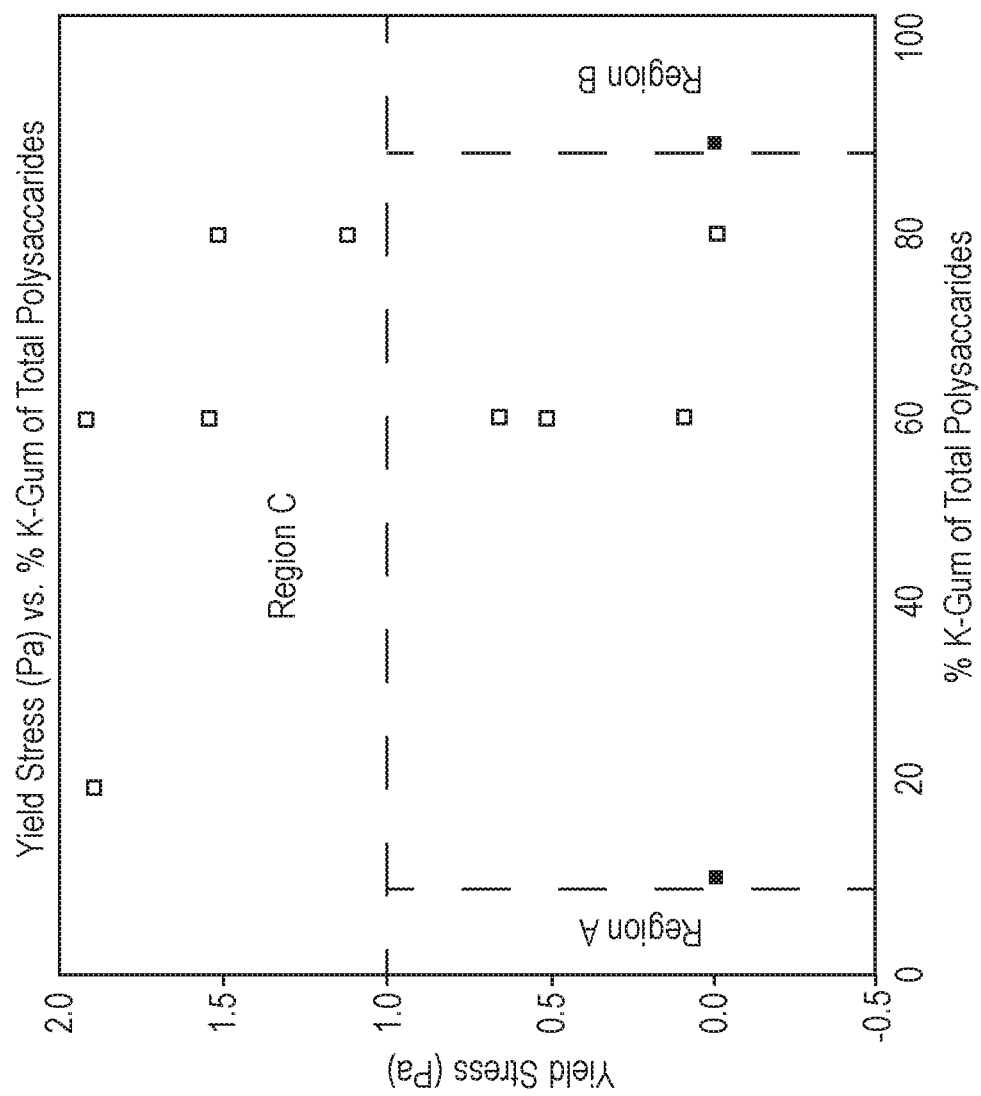
FIG. 1 is a plot of the yield stress of freshening compositions A-Q as a function of the percentage of konjac gum in the structurant system.

Freshening compositions of the present disclosure include a plurality of particles and a structurant system to suspend the particles. The freshening compositions are sprayable and the particles remain suspended for extended periods of time, eliminating the need to shake the product before use.

The freshening compositions may be used in the air or on a surface and/or to remove or reduce the amount of malodors in the air or on a surface and/or to deliver a benefit agent into the air or onto a surface.

The structurant system may be in the form of a polysaccharide system. The polysaccharide system may include a first polysaccharide and a second polysaccharide.

The first polysaccharide comprises xanthan gum. The second polysaccharide is selected from the group consisting of: konjac gum, locust bean gum, and combinations thereof.

The particles may be in the form of benefit agent delivery particles. The benefit agent delivery particles may include a wall material that encapsulates a benefit agent.

A benefit agent may be in the form of a perfume mixture. As used herein, "perfume mixture" comprises at least two perfume raw materials.

When the freshening composition is sprayed through a trigger sprayer, the resulting spray droplets may be characterized by the method described herein as having a normalized D(90) value of less than 2.5, alternatively less than 2.0, alternatively less than 1.5. Alternatively, the spray droplets may be characterized as having a normalized D(4,3) value of less than 2.5, alternatively less than 2.0, alternatively less than 1.5.

In order to be sprayable and/or produce a consumer-acceptable spray pattern, the composition may have a relatively low viscosity under shear conditions typical in a trigger sprayer. The spray shear viscosity may be measured according to the SPRAY SHEAR VISCOSITY PERFORMANCE METHOD as described herein. The spray shear viscosity of the composition may be less than about 0.025 Pa-s, or preferably less than about 0.02 Pa-s, or most preferably less than about 0.01 Pa-s, based on the SPRAY SHEAR VISCOSITY PERFORMANCE METHOD disclosed herein.

The freshening composition may be contained in various types of sprayers, including trigger sprayers, aerosol sprayers, and the like.

The freshening composition may provide a stable suspension of particles, or stated another way, may exhibit a resistance to settling or creaming of the particles. As used herein, stable and unstable refer to the ability of the freshening composition to suspend particles, with stable compositions being able to suspend particles and unstable compositions being unable to suspend particles. The freshening composition may have a phase stability grade of at least 1, alternatively 2 as measured according to the PHASE STABILITY GRADE AT 25° C. TEST METHOD disclosed herein.

In order to maintain a stable suspension of particles, the freshening composition may exhibit a creep recovery ratio when stressed under stress similar to the force levels experienced by the composition when a particle is introduced where the particle has a density different than that of the bulk composition. The creep recovery ratio is measured according to the CREEP RECOVERY RATIO PERFORMANCE METHOD as described herein. The composition may exhibit a creep recovery ratio of at least about 0.1, alternatively at least about 0.2, alternatively at least about 0.3, according to the CREEP RECOVERY RATIO PERFORMANCE METHOD disclosed herein.

In order to maintain a stable suspension of particles, the freshening composition may exhibit a sufficient yield stress. The yield stress of the freshening composition is measured as described herein in the YIELD STRESS PERFORMANCE METHOD. When the composition exhibits a yield stress, the yield stress may be greater than 0 Pa and less than about 1.0 Pa, alternatively about 0.05 Pa to about 0.5 Pa, or according to the YIELD STRESS PERFORMANCE METHOD disclosed herein.

The freshening composition of the present disclosure may exhibit a low level of residue when applied to a dark surface. The residue level of the freshening composition is measured as described in the RESIDUE VALUE PERFORMANCE METHOD. The freshening composition may have a residue value of less than about 8 at 5 sprays, preferably less than about 8 at 15 sprays, or most preferably less than about 8 at 25 sprays according to the RESIDUE VALUE PERFORMANCE METHOD.

The freshening composition may have a residue value of less than about 6 at 5 sprays, preferably less than about 6 at 15 sprays, or most preferably less than about 6 at 25 sprays according to the RESIDUE VALUE PERFORMANCE METHOD disclosed herein.

The total polysaccharide concentration present in the freshening composition may be less than about 0.5 wt. %, or preferably less than about 0.2 wt. %, or preferably less than about 0.1 wt. %, more preferably less than 0.08 wt. %, and most preferably less than 0.06 wt. %. Without wishing to be bound by theory, it is believed that minimizing total polysaccharide levels in the freshening composition diminishes residue and/or lowers spray shear viscosity to optimize the spray characteristics.

Freshening Composition

Freshening compositions of the present disclosure include a plurality of particles and a structurant system to suspend the particles.

The freshening composition may have an ionic strength of less about 0.02 mol/L. Ionic strength is measured according to the following formula:

$$I = \frac{1}{2}\sum_{i=1}^{n} c_i z_i^2$$

where $c_i$ is equal to the molar concentration of ions, i, and had the units mol/L, and where $z_i^2$ is equal to the charge number of the ion. See *Basic Physical Chemistry*, Walter J. Moore, p. 370 (1983).

Particles

The freshening composition may include a plurality of particles. As used herein, a "particle" comprises at least a portion of a solid or semi-solid material. The particle may take various different forms. The particles may be 100 wt. % solid or may be hollow. The particle may include, for example, mesoporous particles, activated carbon, zeolites, benefit agent delivery particle, wax, hydrogel, and/or ground nutshells. Preferably, the particle may include a benefit agent delivery particle.

The plurality of particles may have an average longest projected dimension the range of about 0.1 microns to about 500 microns, alternatively about 1 micrometers to about 100 micrometers, alternatively about 5 micrometers to about 50 micrometers, alternatively less than about 100 micrometers. The longest projected dimension of any single particle within the plurality of particles is taken as the length of the longest linear dimension that can be inscribed entirely within the outer perimeter of the single particle. The average longest projected dimension of the plurality of particles may be taken as the average of the longest linear dimension that can be inscribed entirely within the single particle, across all the particles within the plurality of particles. It would be appreciated by one of ordinary skill in the art that this average may also be reflected by taking the average across a statistically relevant sample of particles from the plurality of particles.

As discussed above, the freshening composition may include a particle in the form of a benefit agent delivery particle. The benefit agent delivery particle may include a wall material that encapsulates a benefit agent. Benefit agent may be referred herein as a "benefit agent" or an "encapsulated benefit agent". The benefit agent may be selected from the group consisting of: a perfume mixture, an insect repellent, a malodor counteractant, and combinations thereof. In one aspect, the perfume delivery technology may comprise benefit agent delivery particles formed by at least partially surrounding a benefit agent with a wall material. The benefit agent may include materials selected from the group consisting of perfume raw materials such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, gamma-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol; silicone oils, waxes such as polyethylene waxes; essential oils such as fish oils, jasmine, camphor, lavender; skin coolants such as menthol, methyl lactate; vitamins such as Vitamin A and E; sunscreens; glycerine; catalysts such as manganese catalysts or bleach catalysts; bleach particles such as perborates; silicon dioxide particles; antiperspirant actives; cationic polymers and mixtures thereof. Suitable benefit agents can be obtained from Givaudan Corp. of Mount Olive, N.J., USA, International Flavors & Fragrances Corp. of South Brunswick, N.J., USA, or Firmenich Company of Geneva, Switzerland. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

The wall material of the benefit agent delivery particle may comprise: melamine, polyacrylamide, silicones, silica, polystyrene, polyurea, polyurethanes, polyacrylate based materials, polyacrylate esters based materials, gelatin, styrene malic anhydride, polyamides, aromatic alcohols, polyvinyl alcohol and mixtures thereof. The melamine wall material may comprise melamine crosslinked with formaldehyde, melamine-dimethoxyethanol crosslinked with formaldehyde, and mixtures thereof. The polystyrene wall material may comprise polyestyrene cross-linked with divinylbenzene. The polyurea wall material may comprise urea crosslinked with formaldehyde, urea crosslinked with gluteraldehyde, polyisocyanate reacted with a polyamine, a polyamine reacted with an aldehyde and mixtures thereof. The polyacrylate based wall materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

The polyacrylate ester based wall materials may comprise polyacrylate esters formed by alkyl and/or glycidyl esters of acrylic acid and/or methacrylic acid, acrylic acid esters and/or methacrylic acid esters which carry hydroxyl and/or carboxy groups, and allylgluconamide, and mixtures thereof.

The aromatic alcohol based wall material may comprise aryloxyalkanols, arylalkanols and oligoalkanolarylethers. It may also comprise aromatic compounds with at least one free hydroxyl-group, especially preferred at least two free hydroxy groups that are directly aromatically coupled, wherein it is especially preferred if at least two free hydroxy-groups are coupled directly to an aromatic ring, and more especially preferred, positioned relative to each other in meta position. It is preferred that the aromatic alcohols are selected from phenols, cresoles (o-, m-, and p-cresol), naphthols (alpha and beta-naphthol) and thymol, as well as ethylphenols, propylphenols, fluorphenols and methoxyphenols.

The polyurea based wall material may comprise a polyisocyanate. The polyisocyanate may be an aromatic polyisocyanate containing a phenyl, a toluoyl, a xylyl, a naphthyl or a diphenyl moiety (e.g., a polyisocyanurate of toluene diisocyanate, a trimethylol propane-adduct of toluene diisocyanate or a trimethylol propane-adduct of xylylene diisocyanate), an aliphatic polyisocyanate (e.g., a trimer of hexamethylene diisocyanate, a trimer of isophorone diisocyanate and a biuret of hexamethylene diisocyanate), or a mixture thereof (e.g., a mixture of a biuret of hexamethylene diisocyanate and a trimethylol propane-adduct of xylylene diisocyanate). In still other embodiments, the polyisocyante may be cross-linked, the cross-linking agent being a polyamine (e.g., diethylenetriamine, bis(3-aminopropyl) amine, bis(hexanethylene)triamine, tris(2-aminoethyl) amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate).

The polyvinyl alcohol based wall material may comprise a crosslinked, hydrophobically modified polyvinyl alcohol, which comprises a crosslinking agent comprising i) a first dextran aldehyde having a molecular weight of from 2,000 to 50,000 Da; and ii) a second dextran aldehyde having a molecular weight of from greater than 50,000 to 2,000,000 Da.

The perfume benefit agent delivery particle may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. The freshening composition may include one or more types of benefit agent delivery particles, for examples two benefit agent delivery particles types, wherein one of the first or second benefit agent delivery particles (a) has a wall made of a different wall material than the other; (b) has a wall that includes a different amount of wall material or monomer than the other; or (c) contains a different amount perfume oil ingredient than the other; (d) contains a different perfume oil; (e) has a wall that is cured at a different temperature; (f) contains a perfume oil having a different cLogP value; (g) contains a perfume oil having a different volatility; (h) contains a perfume oil having a different boiling point; (i) has a wall made with a different weight ratio of wall materials; (j) has a wall that is cured for different cure time; and (k) has a wall that is heated at a different rate.

Preferably, the perfume benefit agent delivery particle has a wall material comprising a polymer of acrylic acid or derivatives thereof and a benefit agent comprising a perfume mixture.

The freshening composition may comprise any amount of particles. With regard to benefit agent delivery particles, the freshening composition may contain from about 0.001 wt. % to about 2.0 wt. %, by weight of freshening composition, of benefit agent contained with the wall material of the benefit agent delivery particle. Or, the freshening composition may contain from about 0.01 wt. % to about 1.0 wt. %, or most preferably from about 0.05 wt. % to about 0.5 wt. %, by weight of freshening composition, of benefit agent contained with the wall material of the benefit agent delivery particle.

With regard to unencapsulated perfume, the freshening composition may include from about 0.001 wt. % to about 2.0 wt. %, or from about 0.01 wt. % to about 1.0 wt. %, or most preferably from about 0.05 wt. % to about 0.5 wt. %, by weight of freshening composition, of unencapsulated perfume.

Structurant System

The freshening composition includes a structurant system having at least one structuring agent. The structuring agent may include one or more biopolymers. Non-limiting examples of such biopolymers include polysaccharides such as polymers of glucose, fructose, galactose, mannose, rhamnose, glucuronic acid and mixtures thereof.

The structurant system may be in the form of a polysaccharide system. Preferable polysaccharides include xanthan gum, glucomannan, galactomannan, and combinations thereof. The glucomannan may be derived from a natural gum such as konjac gum. The galactomannan may be derived from naturals gums such as locust bean gum. Polysaccharides may also include carrageenan. The gums may be modified such as by deacetylation.

The freshening composition may include a polysaccharide system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of konjac gum, locust bean gum, and combinations thereof.

Preferably, the first polysaccharide is xanthan gum and the second polysaccharide is konjac gum.

The first polysaccharide may be present at a level of greater than 10 wt. % and less than 90 wt. %, alternatively about 20 wt. % to about 80 wt. %, alternatively about 40 wt. % to about 60 wt. %, by weight of the polysaccharide system.

The second polysaccharide may be present at a level of about 15 wt. % to about 85 wt. %, alternatively about 20 wt. % to about 80 wt. %, alternatively about 40 wt. % to about 60 wt. %, by weight of the polysaccharide system.

The total concentration of polysaccharide present in the freshening composition may be less than about 0.5 wt. %, or preferably less than about 0.2 wt. %, or preferably less than about 0.1 wt. %, more preferably less than 0.08 wt. %, and most preferably less than 0.06 wt. %. Without wishing to be bound by theory, it is believed that minimizing the total polysaccharide level present in the freshening composition diminishes residue and/or optimizes spray characteristics.

The polysaccharide system may have a weight-average molecular weight in the range of about 10,000 Daltons to about 15,000,000 Daltons, alternatively about 200,000 Daltons to about 10,000,000 Daltons, alternatively about 300,000 Daltons to about 6,000,000 Daltons, alternatively about 300,000 Daltons to about 500,000 Daltons.

The polysaccharide system may be characterized by the average ratio of acetylation. The average ratio of acetylation may be in the range of about 2.0 to about 0.5, preferably in the range of about 1.5 to about 0.5.

The freshening composition may have a total protein level of less than about 100 parts per million (ppm), or less than 50 ppm, or less than 25 ppm, or less than 10 ppm. It may be desirable to limit the total protein level in the freshening composition in order to minimize discoloring of surfaces to which the freshening composition is applied.

Buffering Agent

The freshening composition may include a buffering agent which may be a carboxylic acid, or a dicarboxylic acid like maleic acid, or a polybasic acid such as citric acid or polyacrylic acid. The acid may be sterically stable, and used in this freshening composition for maintaining the desired pH. The buffering agent may also comprise a base such as triethanolamine, or the salt of an organic acid such as sodium citrate. The freshening composition may have a pH from about 3 to about 8, alternatively from about 4 to about 7, alternatively from about 5 to about 8, alternatively from about 6 to about 8, alternatively about 6 to about 7, alternatively about 7, alternatively about 6.5.

Carboxylic acids such as citric acid may act as metal ion chelants and can form metallic salts with low water solubility. The freshening composition may be essentially free of citric acids. The buffer can be alkaline, acidic or neutral.

Other suitable buffering agents for freshening compositions include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl)amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

The freshening compositions may contain at least about 0 wt. %, alternatively at least about 0.001 wt. %, alternatively at least about 0.01 wt. %, by weight of the freshening composition, of a buffering agent. The freshening composition may also contain no more than about 1 wt. %, alternatively no more than about 0.75 wt. %, alternatively no more than about 0.5 wt. %, by weight of the freshening composition, of a buffering agent.

Solubilizer

The freshening composition may contain a solubilizing aid to solubilize any excess hydrophobic organic materials, particularly some malodor reduction materials, perfume materials, and also optional ingredients (e.g., insect repelling agent, antioxidant, etc.) which can be added to the freshening composition, that are not readily soluble in the freshening composition, to form a clear translucent solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

The freshening composition may contain nonionic surfactants, cationic surfactants, and mixtures thereof. The freshening composition may contain ethoxylated hydrogenated castor oil. One type of suitable hydrogenated castor oil that may be used in the freshening composition is sold as Basophor™, available from BASF.

Freshening compositions containing anionic surfactants and/or detergent surfactants may make fabrics susceptible to soiling and/or leave unacceptable visible stains on fabrics as the solution evaporates off of the fabric. The freshening composition may be free of anionic surfactants and/or detergent surfactants.

The freshening composition may comprise from about 0.01 wt. % to about 3 wt. %, preferably from about 0.4 wt. % to about 1 wt. %, more preferably from about 0.1 wt. % to about 0.5 wt. %, most preferably from about 0.1 wt. % to about 0.3 wt. % of solublizing agent. Preferably the solubilizing agent is selected from the group consisting of a surfactant, a solvent and mixtures thereof. Preferably the surfactant comprises a non-ionic surfactant and preferably the solvent comprises an alcohol, a polyol and mixtures thereof.

Surface Tension Reducing Agent

The freshening composition may include a wetting agent that provides a low surface tension that permits the freshening composition to spread readily and more uniformly on hydrophobic surfaces like polyester and nylon. It has been found that the aqueous solution, without such a wetting agent will not spread satisfactorily. The spreading of the freshening composition also allows it to dry faster, so that the treated material is ready to use sooner. Furthermore, a freshening composition containing a wetting agent may penetrate hydrophobic, oily soil better for improved malodor neutralization. A freshening composition containing a wetting agent may also provide improved "in-wear" electrostatic control. For concentrated freshening compositions, the wetting agent facilitates the dispersion of many actives such as antimicrobial actives and perfumes in the concentrated freshening compositions.

Nonlimiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; | and mixtures thereof.

The freshening composition may provide restoration of fabric such as its surface appearance (reduction of wrinkling, improved color appearance, improved or restored fabric shape). Adjunct ingredients that help restore fabric appearance are selected from: water soluble or miscible quaternary ammonium surfactants and water insoluble oil components together with surfactants, emulsifiers, and solvents needed to form a freshening composition that is stable and does not separate. Some nonlimiting preferred emulsifiers are sorbitan esters and sorbitan esters modified with alkylene oxides, such as Tween® 20 (polyoxyethylene (20)sorbitan monolaurate, branched surfactants, like Guerbet alcohols or alkylene oxide modified Guerget alcohols such as Lutensol® XL 70 (Oxirane, 2-methyl-, polymer with oxirane, mono(2-propylheptyl) ether, BASF). Wetting agents aid in spreading components and in reducing foaming of the freshening composition during spraying. Some preferred wetting agents include the class of wetting agents known in the art as superwetters. Not to be bound by theory, super-wetters pack very efficiently at surfaces resulting in an extremely low equilibrium surface tension. Non-limiting examples of such surfactants include Surfynols® like Surfynol® 465 and Surfynol® 104PG 50 (Dow Chemicals).

Water Soluble or Miscible Quaternary Ammonium Surfactant:

Typically, minimum levels of the water soluble quat included in the freshening compositions are at least about 0.01 wt. %, preferably at least about 0.05 wt. %, more preferably at least about 0.1 wt. % even more preferably at least about 0.2 wt. %, based on the total weight of the freshening composition. Typically maximum levels of water soluble quaternary agent included in the freshening composition are up to about 20 wt. %, preferably less than about 10 wt. %, and more preferably less than about 3 wt. % based on the total weight of the freshening composition. Typically, the agent is present in the freshening composition in an amount of about 0.2 wt. % to about 1.0 wt. %.

Specifically, the preferred water soluble quaternary compounds are dialkyl quaternary surfactant compounds. Suitable quaternary surfactants include, but are not limited to, quaternary ammonium surfactants having the formula:

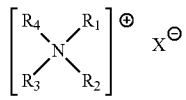

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from about 2 to about 5; X is an anion; and (1) $R_3$ and $R_4$ are each a $C_6$-$C_{14}$ alkyl or (2) $R_3$ is a $C_6$-$C_{18}$ alkyl, and $R_4$ is selected from the group consisting of $C_1$-$C_{10}$ alkyl, $C_1$-$C_{10}$ hydroxy alkyl, benzyl, and —$(C_2H_4O)_xH$ where x has a value from 2 to 5. Preferred asymmetric quaternary compounds are compounds where R3 and R4 are not identical, and preferably one is branched and the other one is linear.

An example of a preferred asymmetric quaternary compound is ARQUAD HTL8-MS where X is a methyl sulfate ion, R1 and R2 are methyl groups, R3 is a hydrogenated tallow group with <5% mono unsaturation, and R4 is a 2-ethylhexyl group. ARQUAD HTL8-MS is available from Akzo Nobel Chemical of Arnhem, Netherlands.

An example of a suitable symmetric quaternary compound is UNIQUAT 22c50 where X is a carbonate and bicarbonate, R1 and R2 are methyl groups, R3 and R4 are C10 alkyl groups. UNIQUAT 22c50 is a registered trademark of Lonza and in North America is available thru Lonza Incorporated of Allendale, N.J.

Another example of a suitable water soluble quaternary compound is BARQUAT CME-35 which is N-Cetyl Ethyl Morpholinium Ethosulfate available from Lonza and having the following structure:

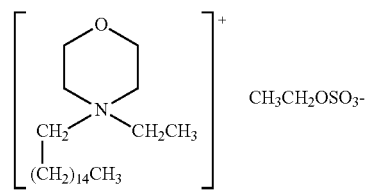

Antimicrobial Compounds

The freshening composition may include an effective amount of a compound for reducing the number of viable microbes in the air or on inanimate surfaces. Antimicrobial compounds are effective on gram negative or gram positive bacteria or fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. The antimicrobial compounds may also be effective at reducing the number of viable viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

A quaternary compound may be used. Examples of commercially available quaternary compounds suitable for use in the freshening composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

Preservatives

The freshening composition may include a preservative. The preservative may be present in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the freshening composition is deposited in order to eliminate odors produced by microorganisms. Instead, it is being used to prevent spoilage of the freshening composition in order to increase the shelf-life of the freshening composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation; 1,2-Benzisothiazolin-3-one; Acticide MBS.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the freshening composition.

Malodor Counteractants

The freshening composition may include other malodor reducing technologies. This may include, without limitation, amine functional polymers, metal ions, cyclodextrins, cyclodextrin deriviatives, polyols, oxidizing agents, activated carbon, and combinations thereof.

Perfume Delivery Technologies

The freshening compositions may comprise one or more perfume delivery technologies that stabilize and enhance the deposition and release of perfume ingredients from treated substrate.

Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

The freshening compositions may comprise from about 0.001 wt. % to about 20 wt. %, or from about 0.01 wt. % to about 10 wt. %, or from about 0.05 wt. % to about 5 wt. %, or even from about 0.1 wt. % to about 0.5 wt. % by weight of the perfume delivery technology. In one aspect, the perfume delivery technologies may be selected from the group consisting of: pro-perfumes, polymer particles, soluble silicone, polymer assisted delivery, molecule assisted delivery, fiber assisted delivery, amine assisted delivery, cyclodextrins, starch encapsulated accord, zeolite and inorganic carrier, and mixtures thereof.

The perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Unencapsulated Perfume

The freshening composition may include unencapsulated perfume comprising one or more perfume raw materials that solely provide a hedonic benefit (i.e. that do not neutralize malodors yet provide a pleasant fragrance). Suitable perfumes are disclosed in U.S. Pat. No. 6,248,135. For example, the freshening composition may include a mixture of volatile aldehydes for neutralizing a malodor and hedonic perfume aldehydes.

Where perfumes, other than the volatile aldehydes in the malodor control component, are formulated into the freshening composition, the total amount of perfumes and volatile aldehydes may be from about 0.015 wt. % to about 2 wt. %, alternatively from about 0.01 wt. % to about 1.0 wt. %, alternatively from about 0.015 wt. % to about 0.5 wt. %, by weight of the freshening composition.

Aqueous Carrier

The freshening composition may include an aqueous carrier. The aqueous carrier which is used may be distilled, deionized, or tap water. Water may be present in any amount for the freshening composition to be an aqueous solution. Water may be present in an amount of about 85 wt. % to 99.5 wt. %, alternatively about 90 wt. % to about 99.5 wt. %, alternatively about 92 wt. % to about 99.5 wt. %, alternatively about 95 wt. %, by weight of the freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the freshening composition due to the addition of these alcohols to such things as perfumes and as stabilizers for some preservatives, the level of monohydric alcohol may about 1 wt. % to about 5 wt. %, alternatively less than about 6 wt. %, alternatively less than about 3 wt. %, alternatively less than about 1 wt. %, by weight of the freshening composition.

Diluents

The freshening composition may also include diluents. Exemplary diluents include dipropylene glycol methyl ether, and 3-methoxy-3-methyl-1-butanol, and mixtures thereof.

Adjuvants

Adjuvants can be added to the freshening composition herein for their known purposes. Such adjuvants include, but are not limited to, water soluble metallic salts, including zinc salts, copper salts, and mixtures thereof; antistatic agents; insect and moth repelling agents; colorants; antioxidants; aromatherapy agents and mixtures thereof.

Sprayable Product

The freshening composition may be packaged in a spray dispenser to form a sprayable product. The sprayable product may be suitable for use in air and on surfaces.

The sprayable product may be configured to deliver a fine mist. The spray dispenser may be configured in various ways, such as a direct compression-type trigger sprayer, a pre-compression-type trigger sprayer, or an aerosol-type spray dispenser. One suitable spray dispenser is the TS800 Trigger Sprayer (Exxon Mobil PP1063, material classification 10003913, Manufacturer: Calmar).

Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition.

Performance Characteristics

It has been found that the freshening compositions of the present disclosure are stable, exhibit a consumer-acceptable spray and have minimal residue. Not wishing to be bound by theory, it is believed that the structurant system of the present disclosure binds uniquely together in a highly effective manner to provide stability at very small polysaccharide concentrations and enable consumer-acceptable spray quality with minimal residue.

The freshening composition may be dispensed from a spray dispenser in the form of spray droplets. A freshening composition of the present disclosure is able to suspend particles, forming a stable freshening composition, while also delivering spray droplets of a relatively uniform and sufficiently small size. Larger and non-uniform spray droplets may deliver an unacceptable appearance to a consumer and may not provide sufficient coverage of the freshening composition in the air or on a surface.

The freshening compositions may also deliver a sufficiently low and consumer acceptable level of residue on a surface after the freshening composition is sprayed and dried onto a surface. For example, preferred freshening compositions of the present disclosure may provide a residue value of less than about 8 at 5 sprays, preferably less than about 8 at 15 sprays, or most preferably less than about 8 at 25 sprays according to the RESIDUE VALUE PERFORMANCE METHOD.

The freshening composition may have a residue value of less than about 6 at 5 sprays, preferably less than about 6 at 15 sprays, or most preferably less than about 6 at 25 sprays according to the RESIDUE VALUE PERFORMANCE METHOD disclosed herein.

A structurant system of the present disclosure may suspend the particles in the freshening composition such that the particles do not float to the top of the freshening composition or sink to the bottom of the freshening composition. For example, freshening compositions of the present disclosure may provide a phase stability grade measured according to the PHASE STABILITY GRADE AT 25° C. TEST METHOD disclosed herein of at least 1, alternatively 2. Stabilizing the particles in the freshening composition eliminates the need to shake the spray dispenser before dispensing the freshening composition. Stabilizing the particles may also help to more evenly distribute the particles throughout the freshening composition so that each spray out of the spray dispenser provides a relatively consistent level of particles.

Rheology Characteristics

Preferable freshening compositions of the present disclosure are able to suspend particles under the stresses that a sprayable product typically experiences. For example, the sprayable product may experience movements such as shaking, tipping, flipping, etc, during shipping, placement on the shelf, and handling by a consumer. The freshening compositions may have a creep recovery ratio as measured according to the CREEP RECOVERY RATIO PERFORMANCE METHOD disclosed herein of at least about 0.1, alternatively at least about 0.2, alternatively at least about 0.3, alternatively at least about 0.4.

The freshening compositions may exhibit a yield stress as measured according to the YIELD STRESS PERFORMANCE METHOD disclosed herein of greater than 0 Pascals (Pa) and less than about 1.0 Pa, or about 0.05 Pa to about 0.5 Pa.

The freshening compositions may exhibit a spray shear viscosity, as measured according to the SPRAY SHEAR VISCOSITY PERFORMANCE METHOD disclosed herein, of less than about 0.025 Pascal seconds (Pa-s), alternatively less than about 0.02 Pa-s, alternatively less than about 0.01 Pa-s.

The freshening compositions of the present disclosure may exhibit a spray shear viscosity of less than about 0.025 Pa-s and either a creep recovery ratio of at least about 0.1 or a yield stress of greater than 0 Pa and less than about 1.0 Pa.

More preferably, freshening compositions of the present disclosure may exhibit a spray shear viscosity of less than about 0.025 Pa-s, a creep recovery ratio of at least about 0.1, and a yield stress of greater than 0 Pa and less than about 1.0 Pa.

The phase-stable sprayable freshening composition comprising suspended particles requires simultaneously three properties: long-term stability, consumer-acceptable spray, and -low residue. This establishes a previously-unsolved contradiction in that long-term stability generally requires high concentrations of structurant while spray and low residue characteristics require low levels of structurant. It was surprising, then, that blending the first polysaccharide with the second polysaccharide within the specification embodied in this specification provides compositions that simultaneous match all three criteria. Without wishing to be bound by theory, it is believed that the first polysaccharide and the second polysaccharide provide for unique intermolecular binding that crosslinks the molecules that allows stability at low levels of structurant to provide for all three properties simultaneously. The compositions, parameters and performance enclosed herein uniquely capture and predict these relationships.

METHODS OF USE

The freshening composition of the present invention can be used by dispersing, e.g., by placing the aqueous solution into a dispensing means, such as a spray dispenser and spraying an effective amount into the air or onto the desired surface or article. An effective amount as defined herein means an amount sufficient to freshen the air or surface and/or neutralize malodor to the point that it is not discernible by the human sense of smell yet not so much as to saturate or create a pool of liquid on an article or surface and so that, when dry, there is no visual deposit readily discernible. Dispersing can be achieved by using a spray device, a roller, a pad, etc.

The present disclosure encompasses the method of dispersing an effective amount of the freshening composition onto household surfaces for reducing malodor and/or freshening the household surfaces. The household surfaces are selected from the group consisting of countertops, cabinets, walls, floors, bathroom surfaces, garbage and/or recycling receptacles, appliances, and kitchen surfaces.

The present disclosure encompasses the method of dispersing a mist of an effective amount of the freshening composition onto fabric and/or fabric articles for reducing malodor and/or freshening the fabric and/or fabric articles. The fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, shower curtains, etc.

The present disclosure encompasses the method of dispersing a mist of an effective amount of the freshening composition onto and into shoes for reducing malodor impression and/or freshening wherein the shoes are not sprayed to saturation.

The present disclosure relates to the method of dispersing a mist of an effective amount of the freshening composition for into the air for freshening and/or to neutralize malodor.

The present disclosure relates to the method of dispersing a mist of an effective amount of the freshening composition onto cat litter, pet bedding and pet houses for freshening and/or to neutralize malodor.

The present disclosure relates to the method of dispersing a mist of an effective amount of the freshening composition onto household pets for freshening and/or to neutralize malodor.

METHODS

Test Method to Quantify Encapsulated Perfume Mixture in Melamine-Formaldehyde or Polyacrylate Particles.

The identity and quantity of each encapsulated perfume raw material (PRM) mixture in benefit agent delivery particles is determined via liquid analysis of solvent-extracts using the analytical chromatography technique of Gas Chromatography Mass Spectrometry with Flame Ionization Detection (GC-MS/FID), conducted using a non-polar or slightly-polar column. The benefit agent delivery particles and the PRM mixture encapsulated therein are physically isolated from the remainder of the freshening composition via filtration, prior to preparing solvent extracts for GC-MS/FID analysis. The known weight of the sample, along with the GC-MS/FID results for the extracted sample and for known calibration standards, are used together to estimate the absolute concentration and weight percentage (wt %) of the encapsulated PRM mixture in the benefit agent delivery particles. This procedure is suitable for the quantitation of PRM mixture encapsulated in melamine-formaldehyde or polyacrylate wall materials, regardless of the presence of additional free (unencapsulated) perfume raw materials in the freshening composition. Benefit agent delivery particles comprising wall materials that are predominantly not of melamine-formaldehyde or polyacrylate chemistry may require some modifications to this method in order to yield an extraction efficiency of at least 95% of the encapsulated perfumes. Such modifications may include alternative solvents or an extended heating and extraction period.

Suitable instruments for conducting these GC-MS/FID analyses includes equipment such as: Hewlett Packard/Agilent Gas Chromatograph model 7890 series GC/FID (Hewlett Packard/Agilent Technologies Inc., Santa Clara, Calif., U.S.A.); Hewlett Packard/Agilent Model 5977N Mass Selective Detector (MSD) transmission quadrupole mass spectrometer (Hewlett Packard/Agilent Technologies Inc., Santa Clara, Calif., U.S.A.); Multipurpose AutoSampler MPS2 (GERSTEL Inc., Linthicum, Md., U.S.A.); and 5%-Phenyl-methylpolysiloxane Column J&W DB-5 (30 m length×0.25 mm internal diameter×0.25 μm film thickness) (J&W Scientific/Agilent Technologies Inc., Santa Clara, Calif., U.S.A.).

One skilled in the art will understand that in order to identify and quantify the PRM mixture in benefit agent delivery particle, the analytical steps may involve: the use of external reference standards; the creation of single-point multi-PRM calibration to generate an average instrumental response factor; and the comparison of measured results against retention times and mass spectra peaks obtained from reference databases and libraries.

Sample Preparation: Benefit agent delivery particles are isolated from the test sample using a syringe filter assembly. The filter membrane is handled carefully using only tweezers with a flat round tip to reduce the potential of damaging the filter membrane. Deionized water (DI water) is used to carefully moisten a 1.2 μm pore size, 25 mm diameter nitrocellulose filter membrane (such as item #RAWP-02500 from EMD Millipore Corporation/Merck, Billerica, Mass., USA), and the wet filter is placed onto the support grate of a Swinnex syringe filter mounting assembly (such as item #SX0002500 from EMD Millipore Corporation/Merck, Billerica, Mass., USA). The filter is centered on the support grate and the edges of the filter and holder are aligned. The sealing o-ring is then added to the filter assembly and the two sections are carefully screwed together while ensuring correct alignment of the filter and o-ring. Filters are used within 24 hrs of being mounted into the Swinnex assembly.

A 2 g sample of the freshening composition being tested is weighed out into a beaker of at least 50 mL capacity, and the weight of the test sample is recorded. Twenty to 40 mL of DI water are added to the test sample and the solution is stirred thoroughly to mix. Using the 60 cc syringe (luer lock is preferred) the sample is filtered through the Swinnex assembly with filter. If blockage of the filter membrane occurs and prevents the filtering of the entire volume of the diluted test sample, then repeat attempts are made using reduced sample weights in iterations (reducing by 0.5 g per iteration), until either a sample mass is found that can be filtered, or until the minimum weight of 0.45 g has been attempted and its filtration has failed. If the minimum weight of 0.45 g of sample cannot be filtered, then the Alternate Preparation Method specified further below is used to prepare that test sample. If a sample mass between 2 g and 0.45 g is successfully filtered, then a 10 mL hexane rinse is subsequently passed through the filter and syringe assembly, and the resultant membrane filter is carefully removed from the mounting assembly and transferred to a 20 mL scintillation vial with a conical seal. The filter is carefully observed to ensure that no tears or holes are present in the filter. If a tear or hole is observed, that filter is disposed of and the test sample is prepared again with a new filter. If the filter is observed to be intact, 10 mL of ethanol is add to the vial and the filter is immersed in this solvent. The vial containing the filter and ethanol is heated at 60° C. for 1 hour then allowed to cool to room temperature for 1 hour. The vial contents are swirled gently to mix, and the ethanol solution is removed from the vial and filtered through a 0.45 µm pore size PTFE syringe filter to remove particulates. This test sample ethanol filtrate is collected in a GC vial, sealed with a cap, and labelled.

The Alternate Preparation Method described below is conducted only if sample filtration has been unsuccessful when following the previously specified preparation method described above. The Alternate Preparation Method is time sensitive and requires that the sample be filtered within 30 seconds of adding the organic solvent to the test sample. For this method, a 2 g sample of the freshening composition being tested is weighed out into a beaker of at least 50 mL capacity, and the weight of the test sample is recorded. Five mL of DI water are added to the test sample and the solution is stirred thoroughly to mix. Premeasured aliquots of 20 mL of isopropyl alcohol and then 20 mL of hexane are rapidly added to the test sample solution and mixed well, then the solution is immediately filtered using the Swinnex filter assembly. This solution must be filtered within 30 seconds after the addition of the organic solvents. After filtering the diluted test sample, the resultant membrane filter is carefully removed from the mounting assembly and transferred to a 20 mL scintillation vial with a conical seal. The filter is carefully observed to ensure that no tears or holes are present in the filter. If a tear or hole is observed, that filter is disposed of and the test sample is prepared again with a new filter. If the filter is observed to be intact, 10 mL of ethanol is add to the vial and the filter is immersed in this solvent. The vial containing the filter and ethanol is heated at 60° C. for 1 hour then allowed to cool and sit at room temperature for 1 hour. The vial contents are swirled gently to mix, and the ethanol solution is removed from the vial and filtered through a 0.45 µm pore size PTFE syringe filter to remove particulates. This test sample ethanol filtrate is collected in a GC vial, sealed with a cap, and labelled.

Instrument Operation: An aliquot of the test sample ethanol filtrate from the GC vial is injected into the GC-MS/FID instrument. A 1 µL injection with a split ratio of from 10:1 is used. If signal or column saturation occurs then a split ratio of up to 30:1 is permissible. For all samples injected, a minimum of 2 solvent rinses are required between sample injections in order to rinse the needle and prevent carryover of material between injections. Analysis conditions include the following: Inlet temperature: 270° C.; Column: J&W DB-5, 30 m length×0.25 mm internal diameter×0.25 µm film thickness Pneumatics: He gas constant flow at 1.5 mL/min; Oven temperatures: 50° C. (0 min), 12° C./min rate, 280° C. (2 min); MSD: Full Scan mode with a minimum range of 40 to 300 m/z (a wider range may be used).

It is important that the final temperature of the system is selected such that it is sufficient to elute all of the perfume materials present in the test sample ethanol filtrate.

Perfume Standards: Three known perfume reference standards are utilized to determine the response factor of the FID for perfume raw materials identification and quantitation. These three reference standards are contained in a Fragrance Allergen Standards Kit available from Restek Corporation, Bellefonte, Pa., USA (item #33105), which contains the Fragrance Allergen Standards: A, B, and C. Samples from each of these 3 known Fragrance Allergen Standards Kit perfume reference standards are transferred without any dilution directly into separate GC vials, sealed, and are respectively labeled as: Std A; Std B; Std C. These known reference standards are injected and analyzed using the same instrument configuration and settings that are used during the analyses of the test sample's ethanol filtrate. If the Restek Fragrance Allergen Standards Kit is unavailable, a substitute may be created by combining at least 20 compounds (with each individual perfume raw material concentration not to exceed 500 ug/mL) from the following list of individual Perfume Raw Material compounds (PRMs) specified below (CAS numbers are given in parentheses): Fragrance Allergen Standard A: α-amylcinnamaldehyde (122-40-7); cinnamal (104-55-2); citral (5392-40-5); 3,7-dimethyl-7-hydroxyoctanal (107-75-5); α-hexylcinnamaldehyde (101-86-0); lilial (80-54-6); lyral (31906-04-4); phenylacetaldehyde (122-78-1). Fragrance Allergen Standard B: α-amylcinnamic alcohol (101-85-9); benzyl alcohol (100-51-6); cinnamyl alcohol (104-54-1); citronellol (106-22-9); eugenol (97-53-0); farnesol (4602-84-0); geraniol (106-24-1); isoeugenol (97-54-1); linalool (78-70-6); 4-methoxybenzyl alcohol (105-13-5); methyl eugenol (93-15-2). Fragrance Allergen Standard C: 4-allylanisole (140-67-0); benzyl benzoate (120-51-4); benzyl cinnamate (103-41-3); benzyl salicylate (118-58-1); camphor (76-22-2); 1,8-cineole (470-82-6); coumarin (91-64-5); limonene (138-86-3); iso-α-methylionone (127-51-5); methyl 2-nonynoate (111-80-8); methyl 2-octynoate (111-12-6); safrole (94-59-7).

Data Analysis: Many libraries and databases of GC-MS retention times and mass spectra of compounds are widely available and are used to identify specific PRMs being tested. Such libraries and databases may include the NIST 14 Gas Chromatography Database and NIST/EPA/NIH Mass Spectral Library version NIST 14 (U.S. Department of Commerce, National Institute of Standards and Technology, Standard Reference Data Program Gaithersburg, Md., U.S.A.); the Wiley Registry of Mass Spectral Data 10th Edition (John Wiley & Sons, Inc., Hoboken, N.J., U.S.A.); and Aroma Office 2D software (GERSTEL Inc., Linthicum, Md., U.S.A.). Within the data generated from the analyses conducted, the FID peaks identified as Perfume Raw Materials (PRMs) based upon retention times and MS results are integrated, (i.e., the area under each peak is determine via integration, to yield a single integration value for each peak), and these values are termed as the "IPRM" value for each given peak. These IPRM values are recorded for use in the additional data calculations specified further below.

The results from the reference standards are used to verify that each PRM in each standard is detected and correctly identified, by comparing the data results obtained versus the information supplied with the reference standards materials. Identification and integration of both isomers, when multiple isomers are noted by the standard reference materials supplied, must be achieved and recorded.

The average relative response factor (RRFavg) for the three known perfume reference standards is calculated according to the equations below, and this value is then utilized to determine the concentration of the encapsulated perfume in the test sample. The data calculations required to determine the quantity of encapsulated perfume involves calculating values according to the following six equations:

The concentration of each perfume standard (Cstd) (in units of g/L), is the sum of all the concentrations of the individual PRMs (Cprm) in each Reference Standard (Std A;

Std B; Std C) according to following equation, such that a Cstd value is calculated for each of the three reference standards:

Cstd (in units of g/L)=(Cprm1+Cprm2=Cprm3+ . . . +Cprm$_n$)

wherein: Cprm1 to Cprm$_n$=the concentration of each respective PRM in the reference standards, based upon the information provided by the supplier of the reference standard materials, and expressed in units of g/L.

The Total Integration (Itotal), is the sum of all the individual PRM integrated values (IPRM) in a given sample, and is calculated according to following equation:

Itotal=(IPRM1+IPRM2+IPRM3+ . . . +IPRM$_n$)

wherein: IPRM1 to IPRM$_n$=the area of the peak for each respective PRM peak in a given sample, (for both test samples and reference standard samples).

The relative response factor (RFF) (concentration in g/L, divided by area), for each of the three perfume reference standards, is calculated according to following equation:

RFF=Cstd/Itotal

The average relative response factor (RFFavg), is calculated according to following equation:

RFFavg=(RFF for Std A+RFF for Std B+RFF for Std C)/3

The weight amount (in grams) of encapsulated perfume in the aliquot of test sample analyzed (Wencap) is calculated according to following equation:

Wencap (in units of grams)=RFFavg*Itotal*0.01 wherein: * is the multiplication mathematical operator.

The weight percentage of a given test sample which is encapsulated perfume (% Encapsulated Perfume), is calculated according to following equation:

% Encapsulated Perfume=(Wencap/the Sample Weight in grams)*100 wherein: * is the multiplication mathematical operator.

A minimum of three replicate samples are prepared and measured for each material tested. The final value reported for each material tested is the average of the % Encapsulated Perfume values measured in the replicate samples of that test material.

Creep Recovery Ratio Performance Method

Measurements for the determination of Creep Recovery Ratio are made with a TA Discovery HR-2 Hybrid Rheometer (TA Instruments, New Castle, Del., U.S.A.), and accompanying TRIOS software version 3.2.0.3877, or equivalent. The instrument is outfitted with a Double Gap Cup (TA Instrument, cat. #546050.901), Double Gap Rotor (TA Instruments, cat. #546049.901) and Split Cover (TA Instruments, cat. #545626.001). The calibration is done in accordance with manufacturer recommendations. A refrigerated, circulating water bath set to 25° C. is attached to the Concentric Cylinder. The Concentric Cylinder temperature is set to 25° C. The temperature is monitored within the Control Panel until the instrument reaches the set temperature, then an additional 5 minutes is allowed to elapse to ensure equilibration before loading sample material into the Double Gap Cup.

The parameters for the Double Gap Cup are as follows: the inside cup diameter is 30.2 mm; the inside bob diameter is 32 mm; the outside bob diameter is 35 mm; the outside cup diameter is 37 mm; the inner cylinder height is 55 mm; the immersed height is 53 mm; the operating gap is 2,000.0 µm; the loading gap is 90,000.0 µm; the Environmental system is Peltier; and a sample volume capacity between 11.4 mL and 15.0 mL.

Samples for testing are obtained without spray dispensing the composition. To load the sample, a minimum of 12 mL of the test sample is added to the Double Gap Cup using a 3 mL plastic syringe. The sample is then allowed to sit for 15 minutes. Any trapped air bubbles are allowed to rise to the surface or otherwise dislodged and removed. The Double Gap Rotor is then lowered to the specified operating gap distance, and data are collected in accordance with the following settings and procedures.

The test sample is subjected to a series of steps conducted in precisely the order specified below, and data are collected during the steps of this in accordance with the instrumental settings specified. All of the steps specified in this series must be conducted, as specified and in the order listed herein regardless of whether or not the final parameter values are derived from any given step. Strict adherence to all the steps specified in there series is important since any given step may create a rheological history in the test sample, which may affect the subsequent steps and data.

The Conditioning Sample Step is conducted using the following instrumental settings: Environmental Control is set with a Temperature of 25° C.; Inherit Set Point is selected as Off; Soak Time is set to 10.0 s; Wait for Temperature is selected as On; Wait For Axial Force is selected as Off; Preshear Options is set with a Perform Preshear selected as Off; Equilibrium is set with a Perform Equilibration selected as On; and Duration is set to 600.0 s.

The First Transient Creep Step is conducted using the following instrumental settings: Environmental Control is set with a Temperature of 25° C.; Inherit Set Point is selected as Off; Soak Time is set to 0.0 s; Wait For Temperature is selected as Off; Test Parameters is set to a Duration of 600.0 s; Stress is selected and set to $1.0e^{-2}$ Pa; Steady State Sensing is selected as Off; Data Acquisition is set with Save Image selected as Off; Fast Sampling is selected as On; Step Termination is set with Limit Checking Enabled selected as On; Equilibrium Enabled is selected as Off.

The Second Transient Creep Step is conducted using the following instrumental settings: Environmental Control is set with a Temperature of 25° C.; Inherit Set Point is selected as Off; Soak Time is set to 0.0 s; Wait For Temperature is selected as Off; Test Parameters is set to a Duration of 1800.0 s; Stress is selected and set to 0.0 Pa; Creep Braking is selected as Off; Steady State Sensing is selected as Off; Data Acquisition is set with Save Image selected as Off; Fast Sampling is selected as On; Step Termination is set with Limit Checking Enabled selected as Off; Equilibrium Enabled is selected as Off.

To calculate the Creep Recovery Ratio, the 'Maximum Strain' is defined as the final Strain value in the First Transient Creep Step; the 'Average Strain Recovery' is defined as the average strain between 150-200 seconds in the Second Transient Creep Streep; and the value of the Creep Recovery Ratio is reported as a unitless decimal value which is calculated in accordance with the following equation:

Creep Recovery Ratio=(Maximum Strain−Average Strain Recovery)/Maximum Strain

Yield Stress and Spray Shear Viscosity Performance Methods

Measurements for the determination of Yield Stress and Spray Shear Viscosity are made with a TA Discovery HR-2 Hybrid Rheometer (TA Instruments, New Castle, Del., U.S.A.) and accompanying TRIOS software version 3.2.0.3877, or equivalent. The instrument is outfitted with a Double Gap Cup (TA Instrument, cat. #546050.901), Double Gap Rotor (TA Instruments, cat. #546049.901) and Split Cover (TA Instruments, cat. #545626.001). The calibration is done in accordance with manufacturer recommendations. A refrigerated, circulating water bath set to 25° C. is attached to the Concentric Cylinder. The Concentric Cylinder temperature is set to 25° C. The temperature is monitored within the Control Panel until the instrument reaches the set temperature, then an additional 5 minutes is allowed to elapse to ensure equilibration before loading sample material into the Double Gap Cup.

The parameters for the Double Gap Cup are as follows: the inside cup diameter is 30.2 mm; the inside bob diameter is 32 mm; the outside bob diameter is 35 mm; the outside cup diameter is 37 mm; the inner cylinder height is 55 mm; the immersed height is 53 mm; the operating gap is 2,000.0 μm; the loading gap is 90,000.0 μm; the Environmental system is Peltier; and a sample volume capacity of between 11.4 mL and 15.0 mL.

Samples for testing are obtained without spray dispensing the composition. To load the sample, a minimum of 12 mL of test sample is added to the Double Gap Cup using a plastic 3 mL syringe. The sample is then allowed to sit for 15 minutes. Any trapped air bubbles are allowed to rise to the surface or otherwise dislodged and removed. The Double Gap Rotor is then lowered to the specified operating gap distance, and data are collected in accordance with the following settings and procedures.

The test sample is subjected to a series of steps conducted in precisely the order specified below, and data are collected during the steps of this series in accordance with the instrumental settings specified. All of the steps specified in this series must be conducted, as specified and in the order listed herein regardless of whether or not the final parameter values are derived from any given step. Strict adherence to all the steps specified in there series is important since any given step may create a rheological history in the test sample, which may affect the subsequent steps and data.

The initial Conditioning Sample Step is conducted using the following instrumental settings: Environmental Control is set with a Temperature of 25° C.; Inherit Set Point is selected as Off; Soak Time is set to 0.0 s; Wait for Temperature is selected as On; Wait For Axial Force is selected as Off; Preshear Options is set with a Perform Preshear selected as Off; Equilibrium is set with a Perform Equilibration selected as On; and Duration is set to 600.0 s.

The Flow Peak Hold Step is conducted using the following instrument settings: Environmental Control is set with a Temperature of 25° C.; Inherit Set Point is selected as Off; Soak Time is set to 0.0 s; Wait for Temperature is selected as Off; Test Parameters is set with a Duration of 600.0 s; Shear Rate is selected and set to 0.01 $s^{-1}$; Inherit initial value is selected as Off; Sampling interval is selected and set to 3.0 s/pt; Controlled Rate Advanced is set with a Motor mode selected as Auto; Data acquisition is set with a End of step selected as Zero torque; Fast sampling is selected as Off; Save image is selected as Off; Step Termination is set with Limit checking Enabled selected as On; Terminate step when is set with Strain (%) selected, >selected, and set to 500%; Equilibrium Enabled is selected as Off.

The Conditioning Sample Step is conducted using the following instrumental settings: Environmental Control is set with a Temperature of 25° C.; Inherit Set Point is selected as Off; Soak Time is set to 10.0 s; Wait for Temperature is selected as On; Wait for axial force is selected as Off; Preshear Options is set with a Perform Preshear selected as Off; Equilibrium is set with a Perform Equilibration selected as On; and Duration is set to 600.0 s.

The Transient Creep Step is conducted using the following instrument settings: Environmental Control is set with a Temperature of 25° C.; Inherit Set Point is selected as Off; Soak Time is set to 0.0 s; Wait For Temperature is selected as Off; Test Parameters is set with a Duration of 600.0 s; Stress is selected and set to 1.0e-3 Pa; Steady State Sensing is selected as Off; Data Acquisition is set with Save Image selected as Off; Fast Sampling is selected as On; Step Termination is set with Limit Checking Enabled selected as On; Terminate Step When is set with Strain (%) selected, >selected, and set to 500%; Equilibrium Enabled is selected as Off.

The second Conditioning Sample Step is conducted using the following instrumental settings: Environmental Control is set with a Temperature of 25° C.; Inherit Set Point is selected as Off; Soak Time is set to 10.0 s; Wait for Temperature is selected as On; Wait For Axial Force is selected as Off; Preshear Options is set with a Perform Preshear selected as Off; Equilibrium is set with a Perform Equilibration selected as On; and Duration is set to 600.0 s.

The Oscillation Amplitude Step is conducted using the following instrumental settings: Environmental Control is set with a Temperature of 25° C.; Inherit Set Point is selected as Off; Soak Time is set to 0.0 s; Wait For Temperature is selected as Off; Test Parameters is set with Frequency selected and set to 1.0 Hz; Logarithmic Sweep is selected, Stress is selected and set to 3.0e-3 Pa to 100.0 Pa; Points Per Decade is set to 10; Controlled Stress Advanced is set with Controlled Stress Type selected as Standard; Data Acquisition is set with Acquisition Mode Correlation selected as On, Transient is selected as Off; Conditioning Time is selected as Time and is set to 3.0 s; Sampling Time is selected as Time and is set to 3.0 s; Save Waveform (Point Display) is selected as On; Number of Points In Waveform is set to 64; Save Image is selected as Off; Use Additional Harmonics is selected as Off; Controlled Flow is set with Torque selected and set to 0.0 uN·m; Step Termination is set with Limit Checking Enabled selected as On; Terminate Step When is set with Oscillation Strain (%) selected, >selected, and set to 500.0%; Equilibrium Enabled is selected as Off.

The third Conditioning Sample Step is conducted using the following instrumental settings: Environmental Control is set with a Temperature of 25° C.; Inherit Set Point is selected as Off; Soak Time is set to 10.0 s; Wait for Temperature is selected as On; Wait For Axial Force is selected as Off; Preshear Options is set with a Perform Preshear selected as Off; Equilibrium is set with a Perform Equilibration selected as On; and Duration is set to 600.0 s.

The Flow Sweep Step is conducted using the following instrument settings: Environmental Control is set with a Temperature of 25° C.; Inherit Set Point is selected as Off; Soak Time is set to 0.0 s; Wait For Temperature is selected as Off; Test Parameters is set with Logarithmic Sweep selected; Shear Rate is selected and set to 1.0e-3 $s^{-1}$ to 1000.0 $s^{-1}$; Points Per Decade is set to 5; Steady State Sensing is selected as On; Max Equilibration Time is set to 45.0 s; Sample Period is set to 5.0 s; % Tolerance is set to 5.0; Consecutive Within is set to 3; Scaled Time Average is selected as Off; Controlled Rate Advanced is set with Motor Mode selected as Auto; Data Acquisition is set with Save Point Display selected as Off; Save Image is selected as Off; Step Termination is set with Limit Checking Enabled selected as Off; Equilibrium Enabled is selected as Off.

The Conditioning End of Test Step is conducted using the following instrument settings: Set Temperature is selected as Off; Set Temperature System Idle (only if axial force control is active) is selected as On.

After collecting data while subjecting the test sample to all of the rheological steps as specified, the Yield Stress value (in units of Pa) is then calculated from the data collected during the Flow Peak Hold Step, in the following way: The data points are plotted as Stress (Pa) on the y-axis against Step Time (s) on the x-axis. The Yield Stress is determined by selecting the "Analysis" tab, then selecting "Signal max" from the Function drop down list and finally selecting "Analyze" in the Commands category.

If the stress at every point in the plot is greater than zero AND the time at 'Max Y' is less than 250 seconds, then the Yield Stress value equals the value of 'Max Y'; if the stress at every point in the plot is greater than zero BUT the time at 'Max Y' is greater than or equal to 250 seconds, then the Yield Stress value equals the value of 'zero'; if the stress at any point in the plot is less than or equal to zero, then the Yield Stress value equals the value of 'zero'.

The Spray Shear Viscosity value is calculated from the data collected during the Flow Sweep Step. Any data points acquired with an applied rotor torque of less than 1 uN·m are discarded; any data points acquired with a strain of less than 300% are also discarded. The remaining data points are plotted as log (shear rate) expressed in units of $s^{-1}$ on the x-axis and log (viscosity) expressed in units of Pa·s on the y-axis. The best-fit straight line is drawn through the last five points of the plot (i.e., the five data points obtained at the five highest shear rates). The Spray Shear Viscosity value is the viscosity value of this line at 1000 $s^{-1}$.

Residue Value Performance Method

For the combination of spray dispenser and freshening composition to be tested, measurements for determining the Residue Value are made using a HunterLab LabScan XE Spectrophotometer and the accompanying EasyMatch QC operating software (all available from Hunter Lab/Hunter Associates Laboratory Inc., Reston, Va., U.S.A.), or equivalent. This instrument is a full-scanning spectrophotometer with a wavelength range of 400 nm to 700 nm and an optical resolution of 10 nm intervals. The instrument measures the amount of light reflected off a surface at a range of wavelengths thereby indicating the color and brightness of the material in a numerical scale colour space system. Within the CIELAB colour space, the three axes are respectively known as: L*, a*, and b* scale axes. Lightness is quantified on the L* axis, wherein L* values range from 0-100 wherein a value of zero represents black and a value of 100 represents white. To determine the Residue Value of a test composition, L* colour measurements are obtained from swatches of dark navy blue wool fabric, both before and after the fabric swatches are spray-treated with the sample composition being tested. The Residue Value is then calculated from the L* measurements obtained.

The spectrophotometer is configured in a 0°/45° optical geometry with the test sample is illuminated with a xenon flash lamp and the reflected light collected via a 15-station fiber optic ring. The HunterLab LabScan XE configuration settings are selected to obtain measurements in terms of the CIELAB tri-axis colour space, with the Illuminant set to D65, and the Observer set to 10°. The Mode Set is selected as 0/45; the Area View is set to 1.75; the Port Size is set to 2.00; the sample cup port plate selected is labeled 1.75-2.00 (largest aperture); the UV Filter is set to Nominal; the Average Method is set to number 4; the Timed Read Method is set to number 4; and the Read Interval is set to 6 seconds.

The instrument is calibrated (standardized) by using a clean standard reference white tile and a clean standard reference black tile on each day that measurements are conducted, with the calibration occurring prior to conducting measurements on test samples.

Fabric swatches serve as the surface substrate upon which the test composition is dispensed for the purposes of this test method. The fabric swatches are squares approximately 20.3 cm in each dimension. The fabric swatches are cut from fabric that is 100% wool worsted gabardine men's suiting material fabric and is dark navy blue in colour (such as Style #541-Navy Worsted Gabardine, available from Test Fabrics Inc. 415 Delaware Avenue, P.O. Box 26, West Pittston, Pa. 18643). For each freshening composition and spray dispenser combination that is being tested, there are two replicate swatches which are each measured on each of four occasions. The four occasions upon which measurements are conducted comprise: an initial measurement prior to any spray treatment (i.e., Initial unsprayed); they are then remeasured after a first treatment (i.e., 5 spray dose); they are then remeasured again after a second treatment (i.e., 15 spray cumulative dose); and then they are finally remeasured yet again after a third treatment (i.e., 25 spray cumulative dose).

All L* measurements, both before and after spray treatments, are conducted on the same planar surface of a given swatch. The reverse-side planar surface of a given swatch is never spray-treated and is never measured by the spectrophotometer. An identifying label or number attached on one surface of the swatch near the fabric edge is helpful to identify the test surface and thus ensure that the surface which is measured initially is the same surface that is then treated, and then also re-measured again after treatment. When measuring any swatch, on any measurement occasion, the fabric is always folded in half and then in half again, such that the folded swatch is four layers thick during the measurement, and is shaped as a square that is approximately 10 cm in each dimension. The fabric is folded such that the surface to be tested is visible on the outside after folding. To conduct a measurement, a 4-layer folded swatch is clamped with the exposed test surface facing downward over the sample port of the spectrophotometer. The instrument is then used to conduct a single L* analysis of the test surface. After that single measurement is taken the swatch is unclamped and flipped over and/or refolded as necessary to reorient the swatch between each measurement, such that each of the four measurements is conducted on a different corner-quadrant of the swatch's test surface. For each replicate swatch on any given measurement occasion, the resultant four L* values obtained are used to calculate the average L* value, which is recorded as the L* value for that swatch on that occasion. The average Initial L* value is recorded for each swatch using the code $L_1 0^*$ for the first replicate swatch, and code $L_2 0^*$ for the second replicate swatch.

After the Initial L* measurements have been acquired, the test surface of each swatch is spray treated. Spray treatment requires a flat plastic board (at least 30 cm×30 cm in dimension), which is secured at a 450 angle (i.e., tilted halfway between vertical and horizontal). The arrangement is such that the upper facing planar surface of the tilted board can be sprayed by a spray jet that is dispensed perpendicular to the board's upper planar surface. A paper towel is placed to cover the upper surface of the board and is secured in place. The fabric swatch to be treated is spread out over the paper towel and secured on the board, with the fabric test surface exposed facing upwards and accessible to be sprayed.

The sample composition to be tested is sprayed onto the fabric swatches, from the spray dispenser device which accompanies the freshening composition. Each fabric swatch being treated is placed on the board and the test surface of the swatch is treated with the test composition by spraying the requisite number of sprays while the spray nozzle is positioned at a distance of 20 cm from the swatch, and while the spray jet is dispensed in the direction perpendicular to the board's planar surface. One fifth of the requisite number of sprays is directed at the centre of the swatch. The other four fifths of the sprays are spread equidistant over the swatch by directing an equal number of the sprays at each centre of a different corner-quadrant. The first treatment dose requires a total of 5 sprays, therefore 1 spray is dispensed to the centre, and four sprays are dispensed to the centres of the corner-quadrants (at 1 spray per corner quadrant). The swatches are dried and measured prior to proceeding to the second treatment. The second treatment achieves a cumulative dose of 15 sprays which includes the 5 sprays already dispensed during the first round of treatment. Therefore the second treatment requires the addition of 10 sprays, 2 of which are dispensed to the centre of the swatch, and 8 of which are dispensed to the centres of the corner-quadrants. The swatches are dried and measured prior to proceeding to the third treatment. The third treatment achieves a cumulative dose of 25 sprays which includes the 15 sprays already dispensed during the first and second treatments. Therefore the third treatment requires the addition of 10 sprays, 2 of which are dispensed to the centre, and 8 of which are dispensed to the centres of the corner-quadrants.

During residue analysis each test sample composition is dispensed from a bottle as a spray plume via a sprayer set to the "spray" position. A new bottle with new trigger sprayer and new nozzle is used for each sample replicate analyzed. The sample is first test sprayed from the sprayer for 1-2 seconds, to ensure that the nozzle is free flowing and not clogged prior to any treatment of fabrics. For the purposes of this test method, one spray from the spray dispenser of the freshening product being tested is defined as one fully complete actuation of the trigger through its full range of motion, with the actuation spanning a time period of approximately 0.7 seconds, and the actuator deployed with a consistent force. Samples analyzed included 'Example Products' which were samples enabled by this invention and prepared in accordance with the details specified in the EXAMPLES section, herein. Samples that were 'Market Products' were shaken thoroughly and removed from the bottle of purchase; Samples that were 'Patent Products' were prepared in accordance with the instructions provided in their respective patents.

After spraying each replicate swatch with the requisite number of sprays required for that treatment occasion, each treated swatch is hung vertically from a rack in the laboratory to air dry for at least 2 hours, while protected from direct sunshine and dust.

After each spray treatment and drying process is completed on each of the three treatment occasions, the treated swatches are each refolded and remeasured in the spectrophotometer in accordance with the folding and measuring procedures specified for the Initial measurements, in order to obtain the L*values for each replicate swatch.

RESIDUE values are calculated for each test sample after each of the three treatment occasions (i.e., doses of 5 sprays, 15 sprays, and 25 sprays), in accordance with the following equation:

$$RESIDUE5 = SQRT((L_1 0^* - L_1 5^*)^2 + (L_2 0^* - L_2 5^*)^2);$$

$$RESIDUE15 = SQRT((L_1 0^* - L_1 15^*)^2 + (L_2 0^* - L_2 15^*)^2);$$

$$RESIDUE25 = SQRT((L_1 0^* - L_1 25^*)^2 + (L_2 0^* - L_2 25^*)^2);$$

wherein; $L_1 0^*$ and $L_2 0^*$ are the average Initial L* values calculated from the untreated fabrics, from the first and second replicate swatches, respectively;

$L_1 5^*$ and $L_2 5^*$ are the average L* values calculated after the first treatment (5 sprays), from the first and second replicate swatches, respectively;

$L_1 15^*$ and $L_2 15^*$ are the average L* values calculated after the second treatment (15 sprays cumulatively), from the first and second replicate swatches, respectively;

$L_1 25^*$ and $L_2 25^*$ are the average L* values calculated after the third treatment (25 sprays cumulatively), from the first and second replicate swatches, respectively;

SQRT is the mathematical function "square root"; and

^2 is the mathematical function "squared".

All RESIDUE values for a test sample are evaluated sequentially in the order of from the lowest number of cumulative sprays dosed to the highest number of cumulative sprays dosed. If a RESIDUE value is less than or equal to 20, then that value is reported and the evaluation proceeds to the RESIDUE value from the next higher dose. If a RESIDUE value for a test sample is greater than 20, this RESIDUE value and all RESIDUE values obtained at a higher number of sprays dosed are assigned a value of 'not measured' in the EXAMPLE tables.

If a test sample forms a stream when sprayed it is considered not sprayable and all RESIDUE values for that test sample are assigned a value of 'stream' in the EXAMPLE tables.

Phase Stability Grade at 25° C. Test Method

Phase stability grades were determined by visual observation of the sample after two weeks of storage, in accordance with the following instructions. A 150 mL sample of product was placed in a clean 8 oz jar (eg VWR, CAT #16195-805, or equivalent) and seal tightly with a metal cap (eg VWR, CAT #89204-934, or equivalent), within one hour after preparation of the sample. The jar was placed in controlled temperature/controlled humidity room set to 25° C. and 60% Relative Humidity. The sealed sample jar was then left quiescent (e.g. no shaking or mixing) for two weeks.

After two weeks, the aged the product was visually assessed and graded for stability. To assess and grade the sample, the observer made every effort to determine whether there was any layer or heterogeneity of turbidity within the sample. This effort included using bright light and adjusting lighting direction as well as altering the direction of observations. A layer may be observed as an area that is more turbid (whiter). A layer may occur near the top surface of the product, and a layer may be very thin. Care was taken to ensure that the product was not be shaken or mixed in any way before or during observation and assessment process. Phase Stability was graded on the following Phase Stability Grading Scale:

A grade of 2 was given if the sample appeared stable as no layer or phase separation was observed and the sample was deemed to be of homogeneous turbidity throughout;

A grade of 1 was given if the sample appeared moderately stable as a possible phase separation layer was observed that was difficult to distinguish and turbidity in the sample was largely unchanged during the two weeks of storage;

A grade of 0 was given if the sample appeared Unstable as an obvious layer or separation within the sample was observed or a significant change in turbidity occurred during the two weeks of storage.

All newly created samples were placed into the storage room within one hour of their preparation. Samples for testing were obtained without spray dispensing the composition.

Samples analyzed included 'Example Products' which were samples enabled by this invention and prepared in accordance with the details specified in the EXAMPLES section, herein.

Samples that were 'Market Products' were shaken thoroughly and removed from the bottle of purchase; Samples that were 'Patent Products' were prepared in accordance with the instructions provided in their respective patents.

Spray D(90) Normalized and Spray D(4,3) Normalized Test Method

Spray droplet volume size distribution measurements comprising Spray D(90) Normalized and Spray D(4,3) Normalized values were determined using a Malvern Spraytec 2000 laser diffraction spray droplet sizing instrument (supplied by Malvern Instruments, Worcestershire, UK), equipped with a 300 mm lens possessing a focal length of the 150 mm, and an Air Purge System (not greater than 14.5 psi). The system was controlled with a computer and software accompanying the instrument, such as the Spraytec software version 3.20 or equivalent, utilizing Mie Theory and Fraunhofer Approximation optical theory. The system was placed in a fume hood for atmospheric control with care taken to place it directly opposite the actuation spray plume trajectory to prevent saturation, with an air flow rate of between 50-70 L/min (60 L/min was the target rate). The distance from the dispensing nozzle orifice to the laser during measurements was 15 cm. During spray droplet analysis, each sample was dispensed from a bottle as a spray plume via a TS-800 trigger sprayer equipped with an actuator delivering 1.3 mL per pull of the trigger, and a nozzle selection type of Fine Mist set to the "spray" position (all supplied by Westrock Company/Silgan, Norcross, Ga., USA). A new bottle with new trigger sprayer and new nozzle was used for each sample replicate analyzed. Lighting conditions were not changed during or between the background control and test sample data collection periods. Light obscuration values below 95% were considered suitable to provide accurate results.

Samples analyzed included 'Example Products' which were samples enabled by this invention and prepared in accordance with the details specified in the EXAMPLES section, herein. Samples that were 'Market Products' were shaken thoroughly and removed from the bottle of purchase; Samples that were 'Patent Products' were prepared in accordance with the instructions provided in their respective patents. All newly created samples were tested within three hours of preparation and were measured at temperatures between 20-22° C. Deionized water was used as a standard reference spray, and was labeled as 'Control Product'. Each sample to be analyzed by this droplet size analysis method was placed into a new spray bottle with nozzle and actuator as specified herein.

Spray measurements were conducted using the following spray SOP instrument configuration: Rapid SOP type was chosen, and the following settings were selected: Hardware Configuration set to "Default", Measurement Type set to "Rapid", Data Acquisition Rate set to "250 Hz", and Lens Type set to "300". Within the Measurement menu: Background set to "2 seconds", Inspection was selected, the box under Output Trigger was Unchecked. Under the Measurement tab "Rapid" was selected, Events Number set to "1", Duration Per Event set to "4000.0", Units set to "ms". Measurement Trigger where Trigger Type set to "Transmission drops to level" and Transmission set to "96", Data Collection where Start is set to "0.0", Units set to "ms", and select "before the trigger" from the drop down menu. On the Advanced tab window all boxes were Unchecked, and Grouping was "no grouping"; The Background Alarms was set to "default values". On the Analysis Tab and under Optical Properties, Particle Set was set to "Water", Dispersant set to "Air", Multiple Scattering Analysis set to "Enable". On the Data Handling tab and under Detector Range was set to "first −8 and last", "No extinction analysis" box was selected, Scattering threshold was set to "1". On the Data Handling/Spray Profile the Path Length was set to "100.0", the Alarm was selected, and the "Use default values" box was checked. On the Additional Properties tab the Curve Fit was set to "no fit", User Size was set to "enable box", the drop down menu as set to "Default". On the Additional Properties/Advanced tab Particle Diameter was set to "0.10" for the minimum and to "900" for the maximum, and Result Type was set to "Volume Distribution". On the Output tab, Export Option was set to "not selected", the Derived Parameter was selected, the Use Averaging Period box was selected and set to "0.0" and "ms". On the Average menu "Average scatter data" was selected. Spray measurements were conducted using the following Spray Procedure: The sample was first test sprayed from the bottle sprayer for 1-2 seconds, to ensure that the nozzle was free flowing and not clogged; the sample in the TS800 sprayer bottle was loaded into the holding device in the front of the Spraytec 2000 system. The spray trigger actuator was pulled with a consistent force and a speed such that the duration of the full actuating stoke was approximately 1 second in length. The spray droplet size data were viewed and saved as "Average Scatter Data".

All measurements were conducting using the instrument configuration procedures specified and, using great care to ensure that the trigger actuator on each sample dispensing bottle was pulled at the same rate for all samples. The value obtained from each Example sample measurement was normalized to the Control sample value in accordance with the following calculations:

$$\text{The value of Spray } D(90) \text{ Normalized} = D(90)_{Example}/D(90)_{Control};$$

$$\text{The value of Spray } D(4,3) \text{ Normalized} = D(4,3)_{Example}/D(4,3)_{Control};$$

wherein:
  D(90) and D(4,3) were values obtained from the instrument software for both the Example and Control samples separately:
  Each of the Spray D(90) Normalized and Spray D(4,3) Normalized values reported for each of the samples in the Example table is the average value calculated from five replicate spray plumes per sample.

Polysaccharide Weight-Average Molecular Weight Test Method

Gel Permeation Chromatography with Multi-Angle Light Scattering Detection (GPC-MALS) is used to measure the weight average molecular weight (Mw) of xanthan gum. A suitable instrument is a Waters 2695 Separation Module (Waters Associates), with a DAWN EOS 18-angle LS and Optilab REX differential RI detectors (Wyatt Technology) connected in series, or equivalent equipment.

Solutions of the gum were prepared by dispersing approximately 10 mg of gum materials in 5 mL of purified HPLC grade water. Sample solutions were mixed and allowed to swell overnight. Each sample was diluted to the concentration of 0.2 mg/ml with 0.1M NaNO3 buffer before the GPC-MALS analysis. Samples were filtered directly into HPLC vials through 0.45 µm Nylon 66 filters (Thermo Fisher Scientific) to remove any microgels or particulate matter.

The separation is performed on two GPC columns such as Waters 7.8×300 mm Ultrahydrogel 2000 and 7.8×300 mm Ultrahydrogel 250 connected in series, or equivalent columns, maintained at 40° C. Components are eluted with a mobile phase of 0.1M NaNO3 at an isocratic flow rate of 1.00 mL/min. 50 µL of the sample is injected for analysis.

Data from the two detectors is collected digitally using suitable software (e.g. Wyatt Astra software). The weight average molecular weight (Mw) is calculated using the Zimm equation. A refractive index increment (dn/dc) of 0.145 ml/g, typical for xanthan gum in aqueous solutions, was used in the calculation.

Polymer Acetylation Test Method

Flow Injection Electrospray Ionization Quadrupole Time-Of-Flight Mass Spectrometry (FI-QTOF-MS) is used to measure the ratio of the acetylated sugar to non-acetylated sugar fragments, and thus determine the relative degree of acetylation modification in the polysaccharide polymer material being tested. In this tandem mass spectrometry analysis the first quadrupole mass analyzer is set at the RF only (broad band) mode so that all ions generated by the electrospray ionization are passed through this first mass filter without selection of a specific precursor ion. All ions after passing the first quadrupole are then fragmented in the second quadrupole. All fragment ions are finally mass separated and detected by the TOF mass analyzer according to their mass-to-charge ratio (m/z). For polymer or gum materials, polysaccharides are fragmented to give structure signature ion m/z 205 (the acetylated sugar) and structure signature ion m/z 163 (the non-acetylated sugar). The ratio of the peak intensity values from these two mass fragments indicates the degree of acetylation present in the material being tested, wherein a higher ratio indicates a higher degree of acetylation.

A sample of any individual polymer raw material to be tested (e.g., a konjac flour, or a xanthan gum) is dissolved at a concentration of 0.5 mg of polymer into 1 ml of water. The aqueous polymer sample solution is mixed and allowed to hydrate overnight. After overnight hydration, the solution is filtered through 0.8 µm pore-size filters (e.g., the Versapor acrylic copolymer membrane disc filter from Pall Corporation of Port Washington N.Y. USA, or equivalent). The filtered solution is placed in an HPLC sample vial for analysis.

Flow Injection-QTOF-MS analysis is conducted using a suitable tandem quadrupole mass spectrometer system with electrospray ionization (such as Q-Tof 2 instruments from the Waters Corporation of Milford Mass. USA, or equivalent). The accompanying software supplied by the instrument manufacturer (such as the Mass Lynx NT version 4.1 data acquisition and processing software from the Waters Corporation, or equivalent) is used to control the instrument and conduct the analysis. The instrumental system is configured with a delivery solvent of 5 mM ammonium acetate/10% acetonitrile in water at a rate of 40 L/min. No columns are used in the instrument configuration. The electrospray capillary voltage is set at 3.5 kV. The first quadrupole mass analyzer is set at the RF only (broad band) mode. To fragment the polymer materials, the second quadrupole with the collision cell energy is set at 70 V so that both signature fragment ions, namely: m/z 205, and m/z 163, are generated. The TOF mass analyzer is scanned from 50 Da to 3000 Da, with a 5 min data acquisition time for each flow injection run. The peak intensity of the m/z 205 fragment (i.e., the acetylated sugar) and the peak intensity of m/z 163 fragment (i.e., the non-acetylated sugar) are acquired. The ratio of these two peak intensity values is calculated and represents the acetylated-to-nonacetylated sugar fragments ratio. This ratio indicates the relative degree of acetylation in the gum or polysaccharide polymer material being tested.

EXAMPLES

Materials for Preparation of Microparticle-Containing Formulations

Deionized Water (M1)

Reverse osmosis deionized (DI) water should contain no more than 100 colony forming units (CFU)/ml, and have at least 50 k-ohm resistivity.

1% K-Gum Solution (M2)

100 grams of 1% K-Gum Solution is prepared to the following composition shown in Table 1.

TABLE 1

| 1% Konjac Gum Solution | |
|---|---|
| DI Water | Balance g |
| Acticide MBS | 0.015 g |
| Nutricol ® XP 3464, FMC corp. (including up to 10.5% moisture) | 1.00 g |

First, 98.95 g of Deionized water is added to a clean mixing 250 mL beaker (Pyrex, Amazon Part Number 574090, or equivalent). Then, 0.015 g of Acticide MBS, biocide product (5% combination of methyl-4-isothiazolin-3-one (MIT) and 1,2-benzisothiazolin-3-one (BIT), Thor Specialties, Inc., 50 Waterview Drive, Shelton, Conn. 06484, USA) is added to the water and mixed with the impellor mixer (IKA RW20, part number AO-50705-00, or equivalent). Then, the mixture is placed under in a Ross Mill bench-top mixer and gradually increasing the mixing speed to 3000 rpm. Then, konjac gum (Nutricol® XP 3464, FMC Corporation, 1735 Market Street, Philadelphia, Pa. 19103) is added into beaker by pouring powder directly on the water surface. Then, the Mill speed is gradually increased to 8000 rpm as the solution thickens. Mix for at least 10 minutes until completely homogenous while lifting the beaker up and down allowing the Mill to touch the top and bottom of the solution. The resulting stock solution is stored in glass bottle, until use. Do not use the stock solution if there is any indication of bacterial growth, such as an overt amine smell or the viscosity decreases by more than 50%, usually about 4 weeks.

1% Xanthan Gum Solution (M3)

100 grams of 1% Xanthan Gum Solution is prepared to the following composition shown in Table 2.

TABLE 2

| 1% Xanthan Gum Solution | |
|---|---|
| DI Water | Balance g |
| Acticide MBS | 0.015 g |
| Xanthan Gum (Archer Daniels | 1.00 g |

TABLE 2-continued

1% Xanthan Gum Solution

Midland Company - ADM.com,
NovaXan Dispersible xanthan gum
or Jungbunzlauer Inc. 7 Wells
Avenue, Newton Centre, MA,
02459, CAS-No. 11138-66-2,
Xanthan gum)
M3.1: JBL Lot# 2526013; or
M3.2: ADM Lot# 170405XXX; or
M3.3: JBL Lot# 2532585; or
M3.4: CPK Lot# 7A5455K First, 98.95 g of Deionized water is added to a clean mixing 250 mL beaker (Pyrex, Amazon Part Number 574090, or equivalent). Then, 0.015 g of Acticide MBS, biocide product (5% combination of methyl-4-isothiazolin-3-one (MIT) and 1,2-benzisothiazolin-3-one (BIT), Thor Specialties, Inc., 50 Waterview Drive, Shelton, Conn. 06484, USA) is added to the water and mixed with the impellor mixer (IKA RW20, part number AO-50705-00, or equivalent). Then, the mixture is placed under in a Ross Mill bench-top mixer and gradually increasing the mixing speed to 3000 rpm. Then, 1.00 g xanthan gum (x-gum source, table) is added into beaker by pouring powder directly on the water surface. Then, the Mill speed is gradually increased to 8000 rpm as the solution thickens. Mix for at least 10 minutes until completely homogenous while lifting the beaker up and down allowing the Mill to touch the top and bottom of the solution. The resulting stock solution is stored in glass bottle, until use. Do not use the stock solution if there is any indication of bacterial growth, such as an overt amine smell or the viscosity decreases by more than 50%, usually about 4 weeks.

ENCAPSYS® Polyacrylate Perfume Microcapsule Slurry, Voyager Zen (M4)

(Total perfume oil 19-23%, Encapsys, LLC, 1401 N. Rankin Street, Appleton, Wis. 54911)

TABLE 3

ENCAPSYS ® Polyacrylate Perfume Microcapsule Slurry

| Ingredient | Mass Percent |
| --- | --- |
| Water | 55.1% |
| Xanthan Gum | 0.20% |
| Sodium Benzoate | 0.25% |
| Potassium Sorbate | 0.25% |
| Perfume Microparticles | 44.20% |
| Free Fragrance | 0.01% |

Magnesium Chloride Anhydrous, 30% Solution (M5)

(30% Magnesium chloride solution, Mineral Research & Development, 5910 Pharr Mill Road, Harrisburg, N.C. 28075)

Polyacrylic Acid (M6)

(KemEcal 142 PG, 100%, Kemira Chemicals, Inc., 1000 Parkwood Circle, Suite 500, Atlanta, Ga. 30339)

Diethylene Glycol (M7)

(Diethylene glycol, 99.6% (100%), Indorama Ventures LLC, 9502 Bayport Boulevard, Pasadena, Tex. 77507)

Silwet* L-7600 (M8)

(Polyalkyleneoxidemethylsiloxane Copolymer, 60-100% (100%), Momentive™, 3500 South State Route 2, Friendly, W. Va. 26146)

Hydroxypropyl Beta Cyclodextrin (CD) Slurry (M9)

(Cavasol W7 HP TL, 40%, Wacker Biosolutions, Hanns-Seidel-Platz 4, 81737 Munchen, Germany)

Ethanol (M10)

(SDA40B/190PF/DNB TBA/137600, 94.3%, Equistar Chemicals, LP, LyondellBasell Tower, 1221 McKinney Street, Houston, Tex. 77252)

Koralone B119 Solution (M11)

(Koralone™ B-119 Preservative, 1,2-Benzisothiazolin-3-one, 19%, The Dow Chemical Company, 100 Independence Mall West, Philadelphia, Pa. 19106)

Citric Acid Solution (M12)

(Citric Acid, 50%, Univar USA Inc., 17425 NW Union Hill Road, Redmond, Wash. 98052)

Carrageenan (M13)

(Cat #J60603, 100%, Alfa Aesar, Thermo Fisher Scientific Chemicals, Inc., 30 Bond Street, Ward Hill, Mass. 01835-8099)

Gellan Gum (M14)

(Kelcogel, Food Grade, Material #10040280, CP Kelco, Inc., 3100 Cumberland Boulevard, Atlanta, Ga. 30339)

Locust Bean Gum (M15)

(Cat #L1135, 100%, Spectrum Chemical Mfg. Corp., 14422 S. San Pedro Street, Gardena, Calif. 90248)

Protocol for Preparation of Microparticle-Containing Formulations

All the examples were prepared as described by the following protocol.

All materials (M1-M12) are combined as listed top-to-bottom in the table for each example, starting with the material on top of the list, follow with second material, followed with third material (and so on) until all the materials are added.

For a specific example, acquire 250 ml glass beaker (Pyrex, Amazon Part Number 574090, or equivalent). Add first material—DI water (M1), at the weight specified in the example.

Insert the mixing element (IKA Propeller stirrer, 4-bladed, or equivalent) into beaker. Turn on element to a sufficient speed to ensure vortex mixing without excessive foam during the balance on the material additions.

Add second material, at the weight specified in the example. Mix the sample for at least one minute to complete mixing.

Add third material, at the weight specified in the example. Mix the sample for at least one minute to complete mixing.

Repeat, by adding and mixing remaining materials one-by-one in sequence until the addition of citric acid (M12), the final material.

Finally, add citric acid (M12) stepwise until obtaining the final, desired pH.

TABLE 4

Freshening Compositions and Preparations for Examples A-H.

| | EXAMPLE | | | | | | | |
|---|---|---|---|---|---|---|---|---|
| | A | B | C | D | E | F | G | H |
| DI Water (M1) | Bal. | Bal. | Bal. | Bal. | Bal. | Bal. | Bal. | Bal. |
| 1% K-gum solution (M2) | 4.5 | 18.00 | 3.00 | 12.00 | 3.00 | 24.00 | 0.50 | 4.50 |
| 1% Xanthan solution (M3.1) | 0.5 | 12.00 | 2.00 | 8.00 | 2.00 | 6.00 | 4.50 | 0.50 |
| PMC Slurry (M4) | 2.31 | 0.23 | 0.23 | 0.46 | 2.31 | 0.23 | 0.23 | 0.23 |
| $MgCl_2$ (M5) | 0.00 | 0.00 | 0.00 | 0.00 | 0.00 | 0.00 | 0.00 | 0.00 |
| Polyacrylic Acid Solution (M6) | 0.19 | 0.19 | 0.19 | 0.19 | 0.19 | 0.19 | 0.19 | 0.19 |
| Diethylene Glycol (M7) | 0.25 | 0.25 | 0.25 | 0.25 | 0.25 | 0.25 | 0.25 | 0.25 |
| Silwet L-7600 (M8) | 0.10 | 0.10 | 0.10 | 0.10 | 0.10 | 0.10 | 0.10 | 0.10 |
| Hydroxypropyl Beta CD (M9) | 1.58 | 1.58 | 1.58 | 1.58 | 1.58 | 1.58 | 1.58 | 1.58 |
| Ethanol (M10) | 3.18 | 3.18 | 3.18 | 3.18 | 3.18 | 3.18 | 3.18 | 3.18 |
| Benzisothiazolinone (M11) | 0.08 | 0.08 | 0.08 | 0.08 | 0.08 | 0.08 | 0.08 | 0.08 |
| Citric Acid (M12) | 0.0 | 0.0 | 0.0 | 0.0 | 0.0 | 0.0 | 0.0 | 0.0 |
| Target pH | 6-7 | 6-7 | 6-7 | 6-7 | 6-7 | 6-7 | 6-7 | 6-7 |

TABLE 5

Performance of Examples A-H

| | EXAMPLE | | | | | | | |
|---|---|---|---|---|---|---|---|---|
| | A | B | C | D | E | F | G | H |
| Yield Stress (Pa) | 0 | 1.925 | 0.091 | 1.548 | 0.094 | 1.123 | 0 | 0 |
| Creep Recovery Ratio | −0.02 | 0.85 | 0.85 | 0.83 | 0.84 | 0.66 | 0.01 | 0.01 |
| Spray Shear Viscosity (Pa · s) | 0.0038 | 0.0565 | 0.0047 | 0.0363 | 0.0050 | 0.0559 | 0.0040 | 0.0033 |
| Phase Stability Grade at 25° C. | 0 | 2 | 2 | 2 | 0 | 2 | 0 | 2 |
| Residue 5* | 0.32 | Stream | 3.49 | Stream | 4.75 | Stream | 0.31 | 1.45 |
| Residue 15* | 2.13 | Stream | 4.25 | Stream | 7.00 | Stream | 0.95 | 0.28 |
| Residue 25* | 3.27 | Stream | 5.74 | Stream | 11.90 | Stream | 1.11 | 0.42 |
| Spray D(90) normalized | 1.86 | 2.43 | 1.73 | 2.50 | 1.03 | 2.15 | 0.90 | 1.04 |
| Spray D(4,3) normalized | 1.41 | 2.76 | 1.30 | 2.53 | 1.21 | 3.49 | 0.94 | 1.12 |

*Residue values reported as "Stream" indicate that the product did not spray as discreet droplets, but as a continuous or semi-continuous stream. This is an unacceptable spray pattern for consumers.

TABLE 6

Freshening Compositions and Preparations for Examples I-Q.

| | EXAMPLE | | | | | | | | |
|---|---|---|---|---|---|---|---|---|---|
| | I | J | K | L | M | N | O | P | Q |
| DI Water (M1) | Bal. | Bal. | Bal. | Bal. | Bal. | Bal. | Bal. | Bal. | Bal. |
| 1% K-gum solution (M2) | 9.00 | 6.00 | 1.00 | 6.00 | 18.00 | 16.00 | 4.00 | 2.00 | 16.00 |
| 1% Xanthan gumsolution (M3.1) | 1.00 | 4.00 | 9.00 | 4.00 | 2.00 | 4.00 | 16.00 | 18.00 | 4.00 |
| PMC Slurry (M4) | 2.31 | 2.31 | 0.23 | 0.23 | 2.31 | 2.31 | 2.31 | 0.23 | 0.23 |

TABLE 6-continued

Freshening Compositions and Preparations for Examples I-Q.

| | EXAMPLE | | | | | | | | |
|---|---|---|---|---|---|---|---|---|---|
| | I | J | K | L | M | N | O | P | Q |
| MgCl$_2$ (M5) | 0.00 | 0.00 | 0.00 | 0.00 | 0.00 | 0.00 | 0.00 | 0.00 | 0.00 |
| Polyacrylic Acid Solution (M6) | 0.19 | 0.19 | 0.19 | 0.19 | 0.19 | 0.19 | 0.19 | 0.19 | 0.19 |
| Diethylene Glycol (M7) | 0.25 | 0.25 | 0.25 | 0.25 | 0.25 | 0.25 | 0.25 | 0.25 | 0.25 |
| Silwet L-7600 (M8) | 0.10 | 0.10 | 0.10 | 0.10 | 0.10 | 0.10 | 0.10 | 0.10 | 0.10 |
| Hydroxypropyl Beta CD (M9) | 1.58 | 1.58 | 1.58 | 1.58 | 1.58 | 1.58 | 1.58 | 1.58 | 1.58 |
| Ethanol (M10) | 3.18 | 3.18 | 3.18 | 3.18 | 3.18 | 3.18 | 3.18 | 3.18 | 3.18 |
| Benzisothiazolinone (M11) | 0.08 | 0.08 | 0.08 | 0.08 | 0.08 | 0.08 | 0.08 | 0.08 | 0.08 |
| Citric Acid (M12) | 0.00 | 0.00 | 0.00 | 0.00 | 0.00 | 0.00 | 0.00 | 0.00 | 0.00 |
| Target pH | 6-7 | 6-7 | 6-7 | 6-7 | 6-7 | 6-7 | 6-7 | 6-7 | 6-7 |

TABLE 7

Performance of Examples I-Q

| | EXAMPLE | | | | | | | | |
|---|---|---|---|---|---|---|---|---|---|
| | I | J | K | L | M | N | O | P | Q |
| Yield Stress (Pa) | 0 | 0.661 | 0 | 0.511 | 0 | 1.900 | 0 | 0 | 1.524 |
| Creep Recovery Ratio | 0.35 | 0.85 | −0.03 | 0.82 | 0.53 | 0.77 | 0.10 | 0.07 | 0.76 |
| Spray Shear Viscosity (Pa · s) | 0.0082 | 0.0118 | 0.0060 | 0.0123 | 0.0208 | 0.0325 | 0.0128 | 0.0115 | 0.0280 |
| Phase Stability Grade at 25° C. | 2 | 2 | 1 | 2 | 2 | 2 | 2 | 2 | 2 |
| Residue 5* | 2.13 | 5.07 | 0.15 | 9.71 | 5.50 | Stream | Stream | 1.07 | Stream |
| Residue 15* | 5.54 | 10.52 | 1.18 | Not Tested | 19.39 | Stream | Stream | 3.54 | Stream |
| Residue 25* | 10.60 | Not Tested | 1.83 | Not Tested | Not Tested | Stream | Stream | 8.26 | Stream |
| Spray D(90) normalized | 1.16 | 1.62 | 1.25 | 1.28 | 1.50 | 2.21 | 1.23 | 1.24 | 1.26 |
| Spray D(4,3) normalized | 1.32 | 1.76 | 1.33 | 1.43 | 2.01 | 2.96 | 1.44 | 1.42 | 1.53 |

*Residue values reported as "Stream" indicate that the product did not spray as discreet droplets, but as a continuous or semi-continuous stream. This is an unacceptable spray pattern for consumers.

The yield stress is an absolute measure of the strength of the structurant system. As discussed above, freshening composition that provides a stable suspension of particles may have a yield stress greater than zero and less than 1.0 Pa, as measured by YIELD STRESS PERFORMANCE METHOD. FIG. 1 illustrates the yield stress of the freshening compositions of Examples A-Q as a function of the wt. % of konjac gum ("K-Gum"), based on the total weight of the structurant system. FIG. 1 also labels the freshening compositions of Examples A-Q as stable or unstable. In FIG. 1, the open squares are stable examples and closed squares are unstable examples. As shown in FIG. 1, freshening compositions that have a wt. % of konjac gum in the range of greater than 10 wt. % to less than 90 wt. %, based on the total weight of the structurant system, and a yield stress greater than zero and less than 1.0 are stable. With an insufficient amount of each polysaccharide (regions A-B), the structurant system is not stable; with too high a concentration of polysaccharide, the system is stable but does not spray (region C).

Figure 2:
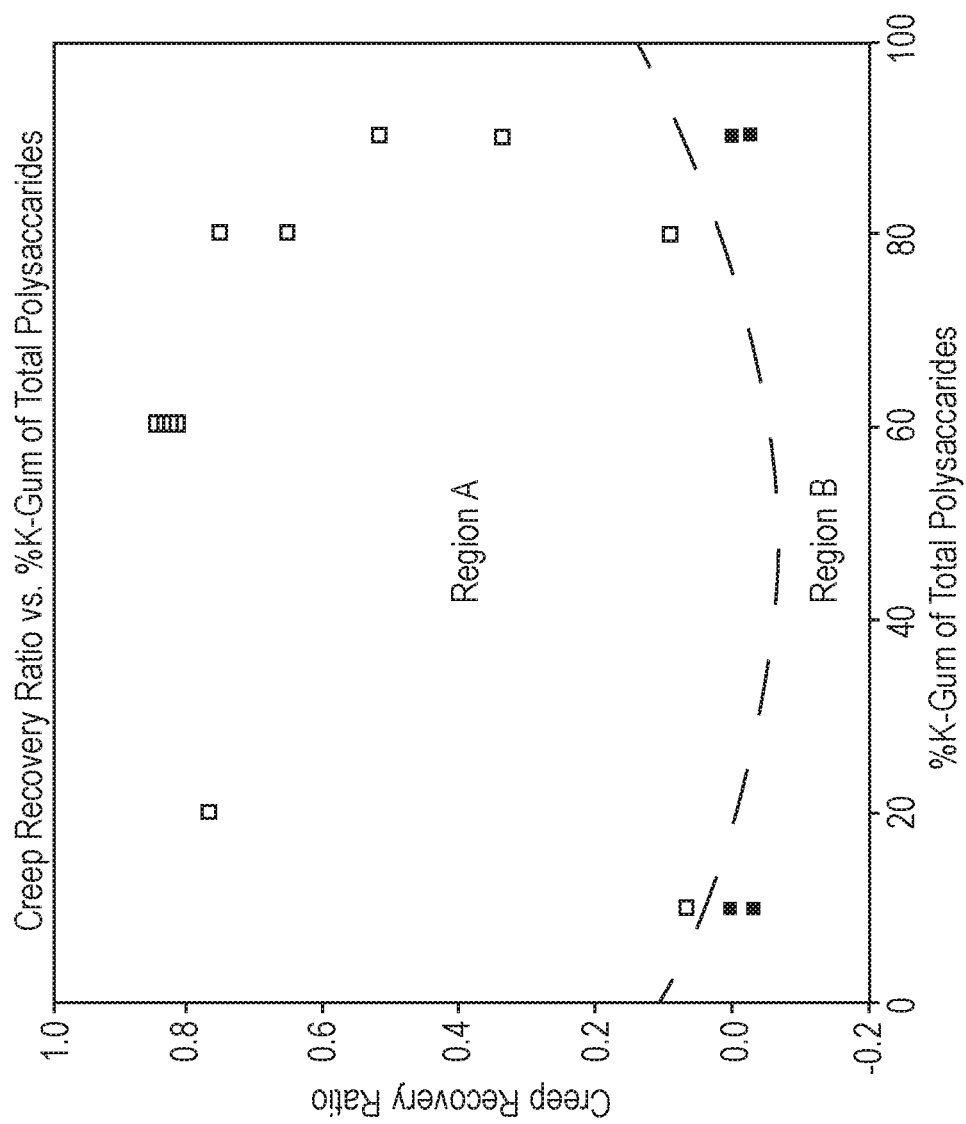
FIG. 2 is a plot of the creep recovery ratio of freshening compositions A-Q as a function of the percentage of konjac gum in the structurant system.

The creep recovery ratio is a relative measure of the strength of the structurant system. Also discussed above, a freshening composition that provides a stable suspension of particles may have a creep recovery ratio, as measured by CREEP RECOVERY RATIO PERFORMANCE METHOD, of at least about 0.1. FIG. 2 illustrates the creep recovery ratio of the compositions of Examples A-Q as a function of the wt. % of konjac gum, based on the total weight of the structurant system. In FIG. 2, the open squares are stable examples and closed squares are unstable examples. As shown in FIG. 2, compositions having a wt. % of konjac gum in the range of greater than 10 wt. % and less than 90 wt. % (sufficient amount of each polysaccharide), based on the total weight of the structurant system, and a creep recovery ratio of greater than 0.1 are stable (region A). Other compositions are unstable (region B)

Figure 3:
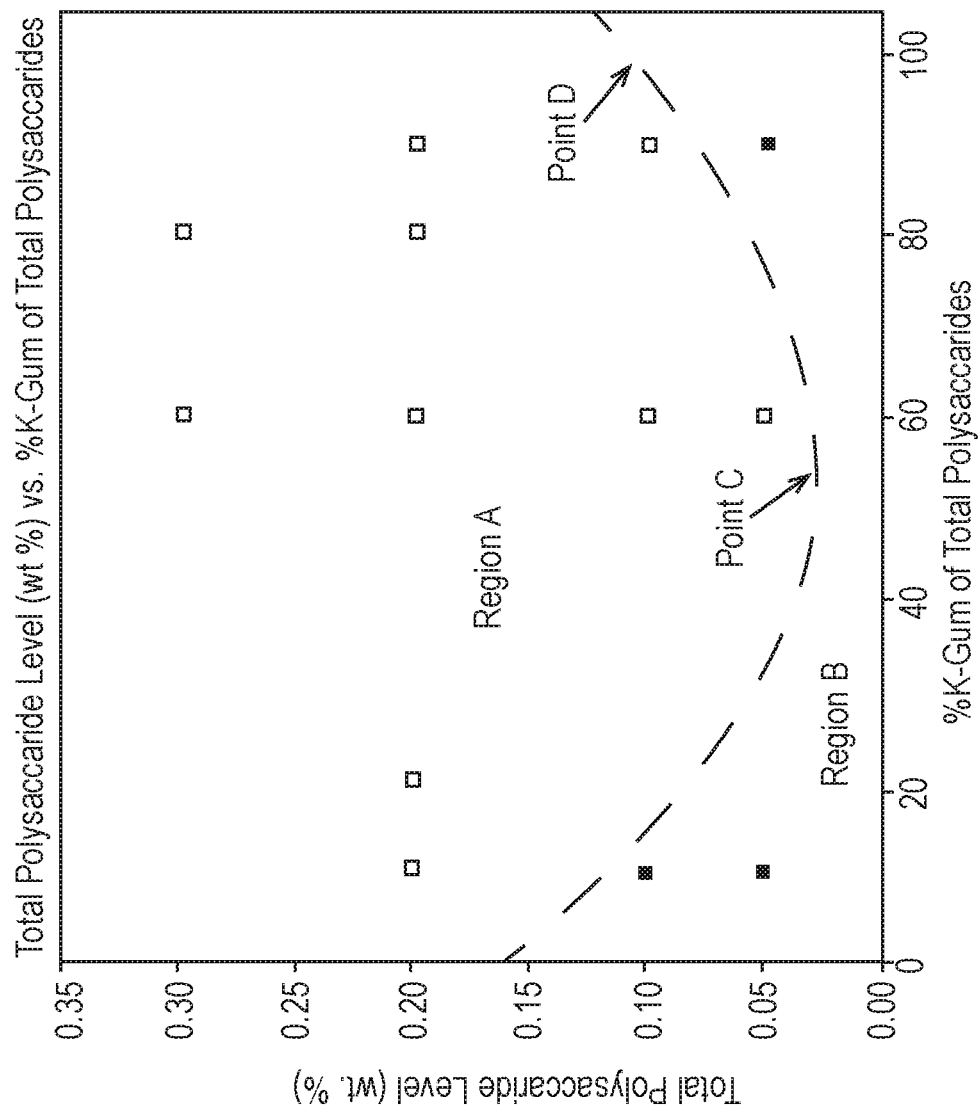
FIG. 3 is a plot of the phase stability performance of freshening compositions A-Q as a function of both the total polysaccharide level of the freshening composition and the percentage of konjac gum in the structurant system.

FIG. 3 illustrates the phase stability performance of Examples A-Q as a function of both total polysaccharide level and % and the konjac gum, based on the total weight of the structurant system. In FIG. 3 open squares represent phase-stable formulations as measure by the PHASE STABILITY at 25° C. PERFORMANCE METHOD, while solid squares represent unstable formulations. FIG. 3, when considered with the data illustrated in the preceding figures, illustrates that to achieve a freshening composition that is stable and sprayable and results in minimal residue, the freshening composition has a total polysaccharide level of less than 0.5 wt. % and the konjac gum is present at a level of greater than 10 wt. % to less than 90 wt. %, based on the total weight of the structurant system (region A—stable; region B—unstable). While not wishing to be bound by theory, when the amount of each polysaccharide is about even, stability is possible at an overall lower concentration of the polysaccharide (point C) but when one polysaccharide is large excess, stability is only possible at am overall higher concentration of polysaccharide (point D).

Figure 4:
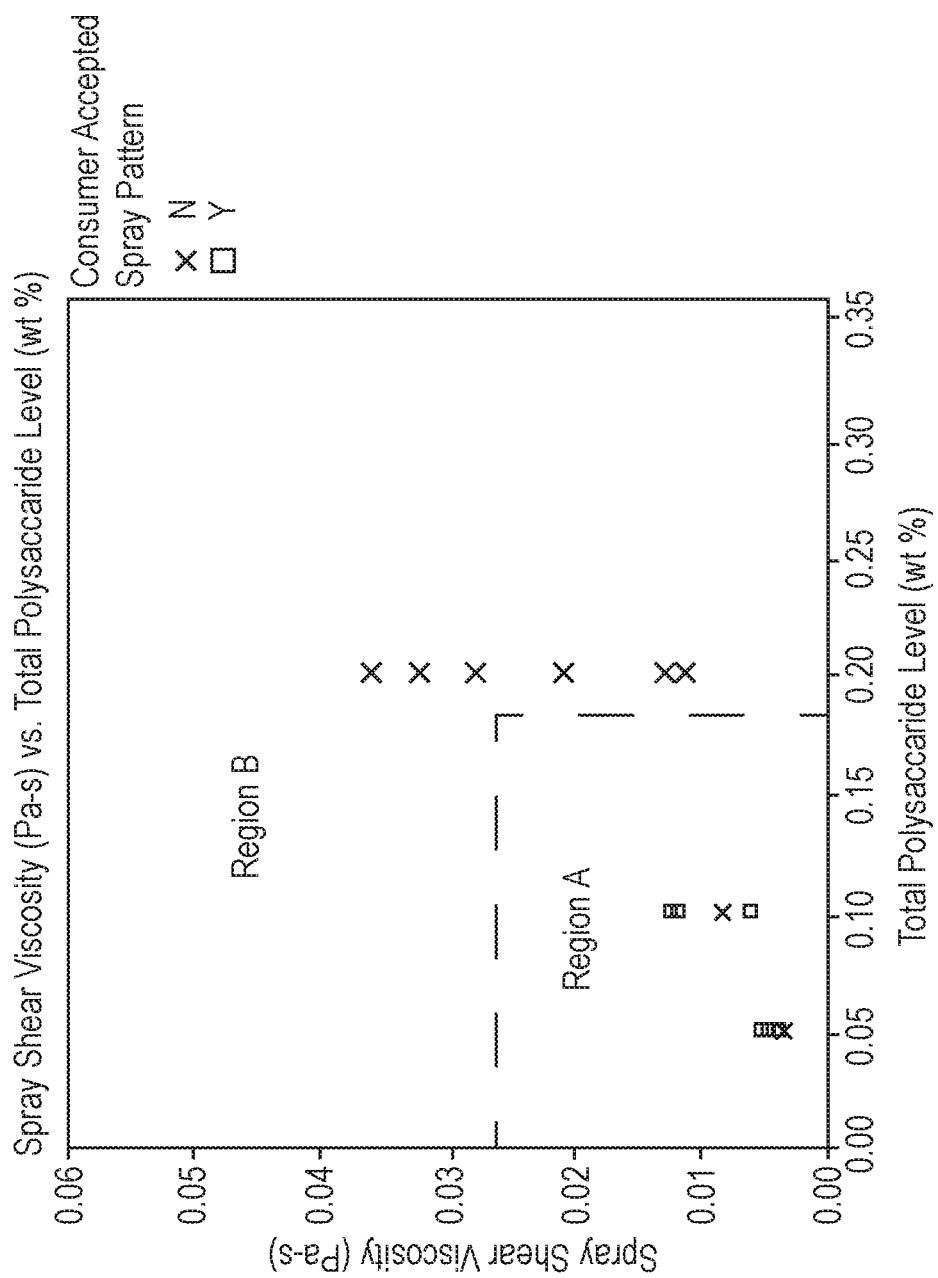
FIG. 4 is a plot of the spray shear viscosity of a freshening composition as a function of the total polysaccharide level of the freshening composition.

Also as discussed above, a sprayable freshening composition may have a spray shear viscosity, as measured by the SPRAY SHEAR VISCOSITY PERFORMANCE METHOD, of less than about 0.025 Pa-s. FIG. 4 illustrates the spray shear viscosity of the compositions of Examples A-Q as a function of the total polysaccharide concentration, based on the total weight of the composition. In FIG. 3, the squares are examples that are sprayable, and the "X" are examples that are not sprayable according to a consumer panel. As shown in FIG. 4, compositions having a total polysaccharide concentration of less than 0.2 wt. % and a spray shear viscosity of less than about 0.025 Pa-s are sprayable (region A), by a large plurality to consumers. So, lower the overall concentrations are favorable to lower shear viscosity and greater consumer acceptance of spray.

Figure 5:
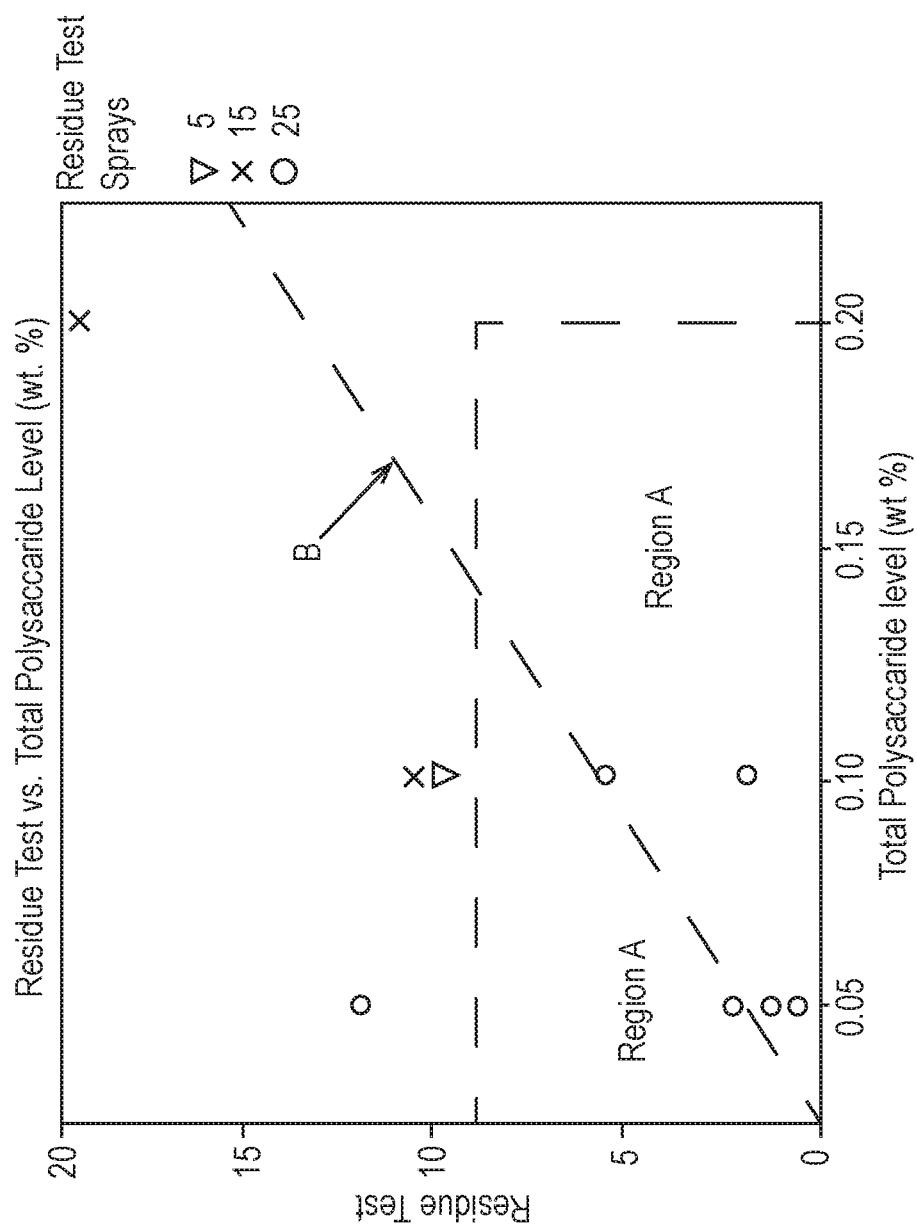
FIG. 5 is a plot of the residue value of a freshening composition as a function of the total polysaccharide level of the freshening composition.

FIG. 5 illustrates residue performance of the freshening compositions of Examples A-Q as a function of total polysaccharide level. As discussed above, a freshening composition providing minimal residue may have a total polysaccharide concentration of less than 0.5 wt. %. FIG. 5 demonstrates that a composition having a total polysaccharide concentration of less than 0.2 wt. %, based on the total weight of the composition, has a residue value of less than 8, as measured by the RESIDUE VALUE PERFORMANCE METHOD, and a composition having a total polysaccharide level of less than 0.1 wt % based on the total weight of the composition, may have a residue value of less than 6 (region A), as measured by the RESIDUE VALUE PERFORMANCE METHOD, when sprayed 25 times. Conversely, compositions with a total polysaccharide level greater than about 0.2 wt. %, based on the total weight of the composition, may have a residue value greater than about 5 when sprayed 25 times, or in some case when sprayed even fewer times. The residue approximately increases in linear fashion with overall polysaccharide level (line B), so that lower overall concentrations are favorable to good residue scores.

TABLE 8

Formulations Table - Alternative Gums (Combined with xanthan gum)

| Examples | Carrageenan | Gellan | Gellan | Locust Bean Gum |
|---|---|---|---|---|
| DI Water (M1) | 91.98 | 89.01 | 89.01 | 89.01 |
| 1% Xanthan gum solution (M3.1) | 2.00 | 2.00 | 3.00 | 2.00 |
| Alternative Gum (M13-M15) | 0.03 (100%) | 3.00 | 2.00 | 3.00 |
| PMC Slurry (M4) | 0.45 | 0.45 | 0.45 | 0.45 |
| pH | 6-7 | 6-7 | 6-7 | 6-7 |

TABLE 9

Performance Table - Alternative Gums

| Examples | Carrageenan | Gellan | Gellan | Locust Bean Gum |
|---|---|---|---|---|
| Yield Stress (Pa) | 0 | 0 | 0 | 0.177 |
| Creep Recovery Ratio | −0.02 | −0.01 | −0.01 | 0.60 |
| Spray Shear Viscosity (Pa · s) | 0.0029 | 0.0026 | 0.0028 | 0.034 |
| Phase Stability Grade at 25° C. | 0 | 0 | 0 | 2 |
| Residue | Not Tested | Not Tested | Not Tested | Not Tested |
| Spray D(90) | Not Tested | Not Tested | Not Tested | Not Tested |
| Spray D(50) | Not Tested | Not Tested | Not Tested | Not Tested |

Table 9 demonstrates the performance various gums as the first polysaccharide and the second polysaccharide.

Without wishing to be bound by theory, it is believed that a good structurant system requires that the first polysaccharide and the second polysaccharide bind strongly to each other, which is only possible with specific blends. The data in Tables 4-7 demonstrate that xanthan gum and konjac gum bind strongly, when within the compositional limits established in the specification. The data in Tables 8-9 demonstrate that xanthan gum and locust bean gum bind strongly and are suitable for the freshening compositions, as evident by the non-zero yield stress, large creep recovery ratio and low spray shear viscosity. The data in Tables 8-9 demonstrate that xanthan gum and carrageenan and/or xanthan gum and gellan gum do not bind strongly, as evident by lack of yield stress and negative creep recovery ratio.

TABLE 10

| Examples | HERO ™ Clean product* | WONDER FRESH ™ Sky product** | WONDER FRESH ™ Spring product** | Example I of WO 2013034871 | Example II of WO 2013034871 |
|---|---|---|---|---|---|
| Yield Stress (Pa) | 0 | 0 | 0 | 0 | 0 |
| Creep Recovery Ratio | 0.01 | −0.01 | −0.00 | 0.95 | 0.01 |
| Spray Shear Viscosity (Pa · s) | 0.0049 | 0.0152 | 0.0165 | 0.117 | 0.0128 |
| Phase Stability Grade at 25° C. | 0 | 0 | 0 | 2 | 0 |
| Residue 5 | 1.48 | 1.37 | n/a | 2.76 | 1.22 |
| Residue 15 | 1.07 | 1.34 | n/a | 6.75 | 4.44 |
| Residue 25 | 1.91 | 2.02 | n/a | 9.39 | 6.72 |
| Spray D(90) normalized | 0.95 | 0.94 | 0.96 | n/a | n/a |
| Spray D(4.3) normalized | 0.97 | 0.96 | 1.00 | n/a | n/a |

*Available at: www.hero-clean.com; www.amazon.com; or www.target.com
**Available at www.bedbathandbeyond.com Commercially available sprayable compositions having particles in the form of benefit agent delivery particles were purchased, including HERO™ Clean, WONDER FRESH™-Sky, and WONDER FRESH™-Spring products. The performance of the commercially available products were tested and the results are shown in Table 10. Moreover, WO2013/034871 teaches sprayable compositions that comprise particles. Examples I and II of WO2013/034871 were reproduced. As shown in Table 10, none of the commercially available compositions or Example II of WO2013/034871 that comprise particles have a yield stress of greater than 0 Pa, nor a creep recovery ration of at least 0.1. Correspondingly, these commercially available products do not suspend the particles present in the composition as shown by the phase stability grade according to the Phase Stability Grade at 25° C. Test Method Although Example I of WO2013/034871 has a Creep Recovery Ratio greater than about 0.1 and a shear viscosity, it has a residue value as measured by the RESIDUE VALUE PERFORMANCE METHOD greater than about 5 after 15 and 25 sprays, meaning that residue is unacceptable to consumers when sprayed on dark fabrics. Further, Example I of WO2013/034871 has a spray shear viscosity as measured by the SPRAY SHEAR VISCOSITY PERFORMANCE METHOD of greater than 0.025 Pa-s, indicating that this product will not give acceptable spray pattern in trigger-type sprayers.

TABLE 11

Freshening Composition and Preparations of Examples R and S

| | R | S |
|---|---|---|
| DI Water (M1) | Bal. | Bal. |
| 1% K-gum solution (M2) | 2.20 | 2.00 |
| 1% X-gum solution (M3.1) | 2.20 | 2.00 |
| PMC Slurry (M4) | 0.10 | 0.40 |
| MgCl₂ (M5) | 0.00 | 0.00 |
| Polyacrylic Acid Solution (M6) | 0.19 | 0.19 |
| Diethylene Glycol (M7) | 0.25 | 0.25 |
| Silwet L-7600 (M8) | 0.10 | 0.10 |
| Hydroxypropyl Beta CD (M9) | 1.58 | 1.58 |
| Ethanol (M10) | 3.18 | 3.18 |
| Koralone B-119 (M11) | 0.08 | 0.08 |

TABLE 11-continued

Freshening Composition and Preparations of Examples R and S

| | R | S |
|---|---|---|
| Citric Acid (M12) | 0.00 | 0.01 |
| pH | 6-7 | 5-6 |

TABLE 12

Performance of Examples R and S

| | R | S |
|---|---|---|
| Yield Stress (Pa) | 0.057 | 0.105 |
| Creep Recovery Ratio | 0.70 | 0.83 |
| Spray Shear Viscosity (Pa · s) | 0.0041 | 0.0035 |
| Phase Stability Grade at 25° C. | 2 | 2 |

TABLE 13

Freshening Composition Examples T Through V

| EXAMPLE | T | U | V |
|---|---|---|---|
| DI Water (M1) | Bal. | Bal. | Bal. |
| 1% K-gum solution (M2) | 3.00 | 3.00 | 3.00 |
| 1% Xanthan gum solution (M3) | 2.00 (M3.2) | 2.00 (M3.3) | 2.00 (M3.4) |
| PMC Slurry (M4) | 1.36 | 1.36 | 1.36 |
| MgCl₂(M5) | 0.00 | 0.00 | 0.00 |
| Polyacrylic Acid Solution (M6) | 0.19 | 0.19 | 0.19 |
| Diethylene Glycol (M7) | 0.25 | 0.25 | 0.25 |
| Silwet L-7600 (M8) | 0.10 | 0.10 | 0.10 |
| Hydroxypropyl Beta CD (M9) | 1.58 | 1.58 | 1.58 |
| Ethanol (M10) | 3.18 | 3.18 | 3.18 |
| Benzisothia-zolinone (M11) | 0.08 | 0.08 | 0.08 |
| Citric Acid (M12) | 0.00 | 0.00 | 0.00 |
| Target pH | 6-7 | 6-7 | 6-7 |

TABLE 14

Performance of Examples T Through V

| EXAMPLE | T | U | V |
|---|---|---|---|
| Yield Stress (Pa) | 0.000 | 0.000 | 0.018 |
| Creep Recovery Ratio | 0.383 | 0.005 | 0.141 |
| Spray Shear Viscosity (Pa · s) | 0.00546 | 0.00455 | 0.00494 |
| Phase Stability Grade at 25° C. | 2 | 0 | 2 |
| Spray D(90) normalized - Prefresh | 1.34 | 1.05 | 0.93 |
| Spray D(4.3) normalized - Prefresh | 1.43 | 1.08 | 0.96 |
| Molecular Weight (KDa) | 12,837 | 3,035 | 5,407 |
| Avg Ratio Acetylation | 5.20 | 2.60 | 0.99 |

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as "1 to 10" is intended to mean "1, 2, 3, 4, 5, 6, 7, 8, 9, 10."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sprayable product comprising a spray dispenser and a freshening composition disposed in the spray dispenser, the freshening composition comprising:

a plurality of particles comprising a plurality of benefit agent delivery particles having a benefit agent and a wall material encapsulating the benefit agent, wherein the composition comprises from about 0.001% to about 1.0%, by weight of the composition, of the encapsulated benefit agent;

a polysaccharide system comprising a first polysaccharide and a second polysaccharide, wherein the first polysaccharide is xanthan gum, and wherein the second polysaccharide is selected from the group consisting of konjac gum, locust bean gum, and combinations thereof, wherein the xanthan gum has an average ratio of acetylation in the range of about 2.0 to about 0.5; and an aqueous carrier;

wherein the composition has a yield stress of greater than 0 Pa and less than about 1.0 Pa, as measured by the YIELD STRESS AND SPRAY SHEAR VISCOSITY TEST METHOD described herein, wherein the first polysaccharide is present at a level of 40 wt. % to 60 wt. %, by weight of the polysaccharide system; and wherein the total polysaccharide level of the composition is less than about 0.2 wt. % by weight of the composition.

2. The composition of claim 1, wherein the polysaccharide system has a weight-average molecular weight in the range of about 10,000 Daltons to about 15,000,000 Daltons.

3. The composition of claim 1, wherein the wall material of the plurality of benefit agent delivery particles comprises one or more of cationic, nonionic, and/or anionic coatings.

4. The composition of claim 1, wherein the wall material of the plurality of benefit agent delivery particles are a material selected from the group consisting of: a polymer of acrylic acid or derivatives thereof, melamine formaldehyde, polyuria, and mixtures thereof.

5. The composition of claim 1, wherein the benefit agent of the plurality of benefit agent delivery particles are a material selected from the group consisting of: a perfume mixture, a malodor counteractant, an antimicrobial agent, an insect repellant, and combinations thereof.

6. The composition of claim 1, wherein the plurality of benefit agent delivery particles have an average longest projected dimension of about 0.1 μm to about 500 μm.

7. The composition of claim 1, further comprising a surface tension reducing agent, wherein the surface tension reducing agent is selected from the group consisting of: quaternary ammonium compounds, non-ionic surfactants, anionic surfactants, silicon compounds and combinations thereof.

8. The composition of claim 1, further comprising a malodor counteractant, wherein the malodor counteractant is selected from the group consisting of: polyols, cyclodextrin and derivatives thereof, amine functional polymers, aldehydes, and combinations thereof.

9. The composition of claim 1, further comprising an antimicrobial agent selected from the group consisting of quaternary ammonium compounds, benzoisothiazolinone compounds, and combinations thereof.

10. The composition of claim 1, wherein the composition further comprises from about 0.015% to about 1.0% of unencapsulated perfume, by weight of the composition.

11. The composition of claim 1, wherein the composition has an ionic strength of less than about 0.02 mol/L.

12. A method of freshening comprising the step of spraying the composition of claim 1 onto a surface.

* * * * *